(12) United States Patent
Shinn et al.

(10) Patent No.: US 6,900,059 B1
(45) Date of Patent: May 31, 2005

(54) READER FOR CONDUCTING ASSAYS

(75) Inventors: Alan Shinn, Berkeley, CA (US); Chiko Fan, San Jose, CA (US); Elias R. Elias, Milton, MA (US); Thomas J. Novitsky, Teaticket, MA (US); Michael Dawson, East Falmouth, MA (US); Keith Richardson, Woods Hole, MA (US)

(73) Assignee: Associates of Cape Cod, Inc., East Falmouth, MA (US)

( * ) Notice: Subject to any disclaimer, the term of this patent is extended or adjusted under 35 U.S.C. 154(b) by 508 days.

(21) Appl. No.: 09/721,973

(22) Filed: Nov. 27, 2000

Related U.S. Application Data

(60) Provisional application No. 60/167,618, filed on Nov. 26, 1999.

(51) Int. Cl.[7] ............................................. G01N 21/27
(52) U.S. Cl. ..................... 436/43; 436/164; 422/82.11; 422/82.05; 422/64
(58) Field of Search ................. 422/64, 82.05, 422/82.11; 436/43, 164, 172; 356/73, 435, 440; 385/12, 146

(56) References Cited

U.S. PATENT DOCUMENTS

| | | | |
|---|---|---|---|
| 3,748,044 A | 7/1973 | Liston | 356/180 |
| 3,882,318 A | 5/1975 | Mioduski | 250/576 |
| 4,406,547 A | 9/1983 | Aihara | |
| 4,412,742 A | 11/1983 | Lloyd | |
| 4,676,951 A | 6/1987 | Armes et al. | 422/65 |
| 4,784,947 A | 11/1988 | Noeller | 435/33 |
| 4,835,110 A | 5/1989 | Seymour et al. | 436/517 |
| 4,873,633 A | 10/1989 | Mezei et al. | 364/413.08 |
| 4,889,815 A | 12/1989 | Bradwell et al. | 436/517 |
| 4,936,682 A | 6/1990 | Hoyt | 356/414 |
| 5,100,805 A | 3/1992 | Ziege et al. | 436/517 |
| 5,162,236 A | 11/1992 | Pang et al. | 436/517 |
| 5,223,219 A | 6/1993 | Subramanian et al. | 422/55 |
| 5,305,093 A | 4/1994 | Dosmann | 356/435 |
| 5,337,139 A | 8/1994 | Shirasawa | 356/73 |
| 5,402,241 A | 3/1995 | Jeannotte et al. | 356/436 |
| 5,415,839 A | 5/1995 | Zaun et al. | |
| 5,424,840 A | 6/1995 | Moore et al. | 356/410 |
| 5,439,647 A | 8/1995 | Saini | |
| 5,745,231 A | 4/1998 | Groger et al. | |

Primary Examiner—Jeffrey R. Snay
(74) Attorney, Agent, or Firm—Lowrie, Lando & Anastasi, LLP

(57) ABSTRACT

An analytical device that can be used to conveniently and accurately assay plural vessels. In one exemplary embodiment, a pair of LED sources provides illumination through a pair of radial waveguides to plural vessels arranged in a pair of substantially concentric and circular rows about the LED sources. A light pipe receives light transmitted through a vessel from each radial waveguide and reflects the received light downward to a single printed circuit board that contains a photodiode for each light pipe, as well as processing circuitry. The first LED source/radial waveguide optical is used to confirm the presence of a vessel, and the second is used to perform, e.g., turbidometric and/or calorimetric assays upon an analyte within the vessel. The vessel is incubated in a vessel support that includes a heat conducting base and a heat insulating cover. Heat is supplied by a DC heater.

84 Claims, 23 Drawing Sheets

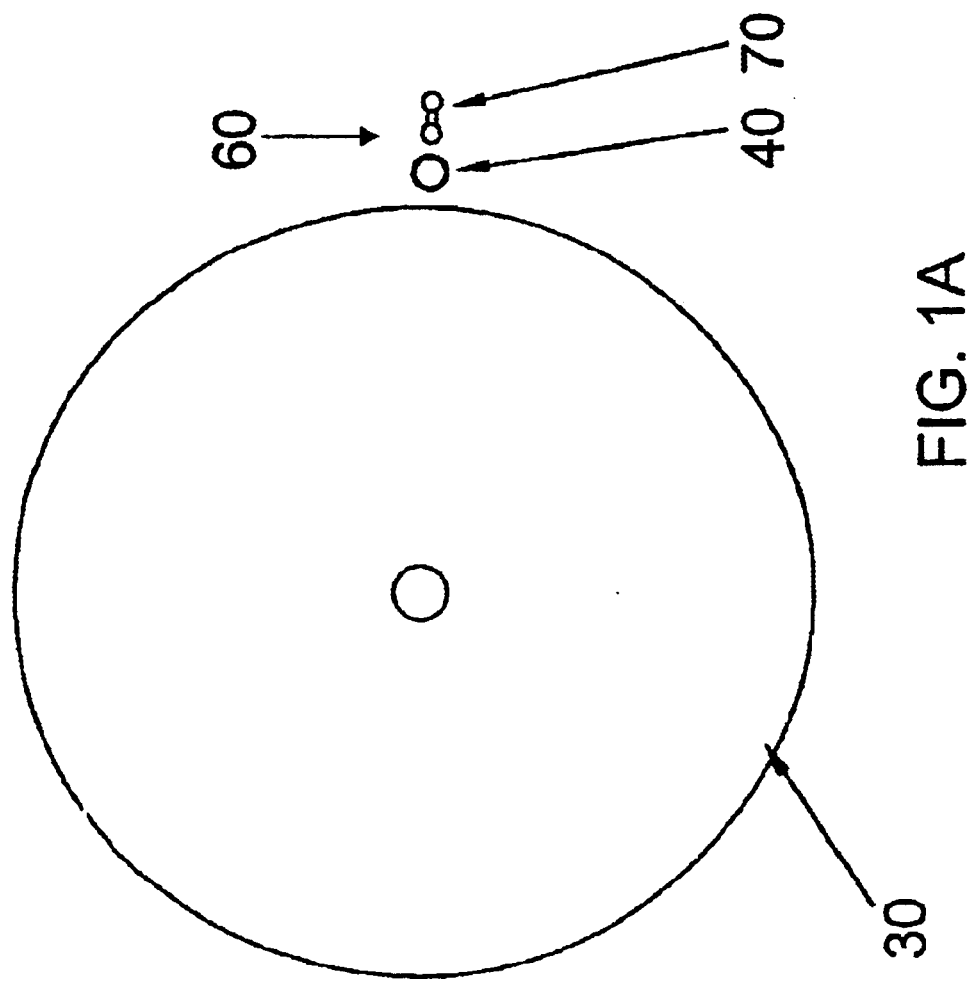

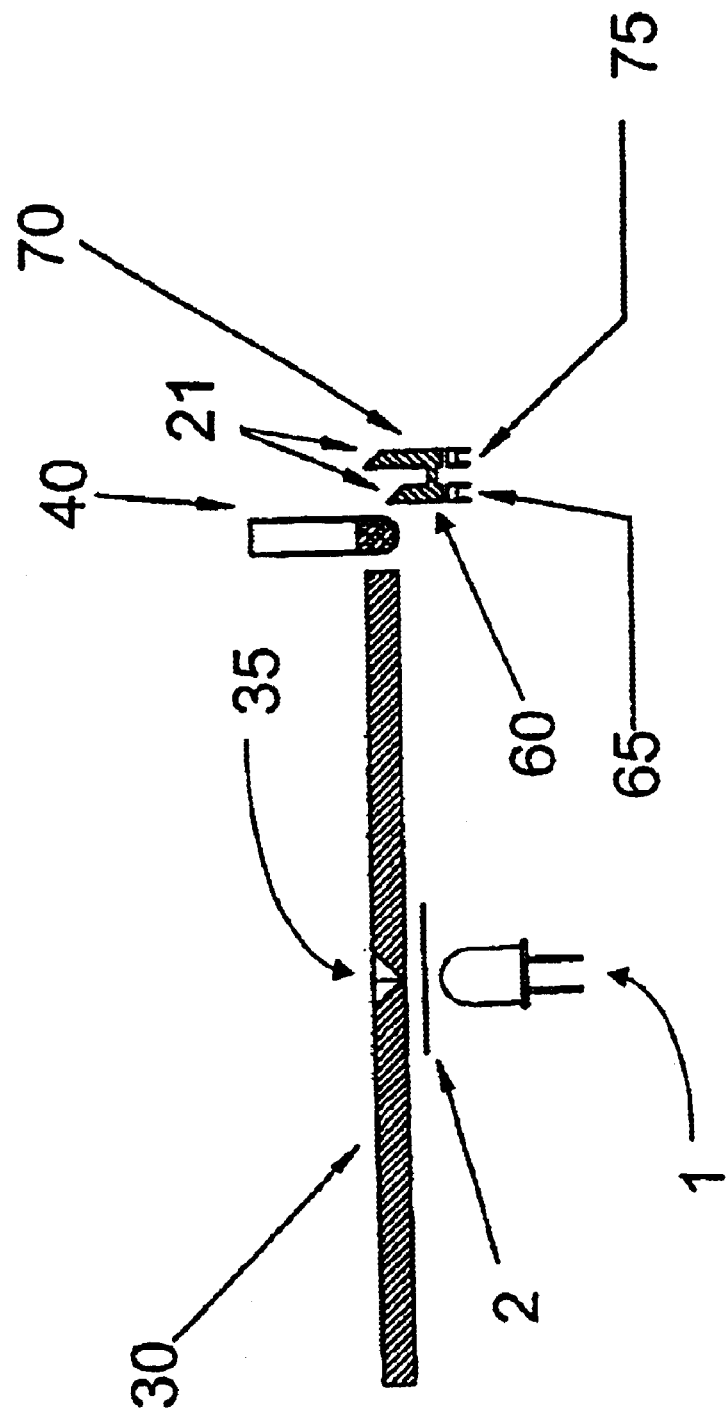

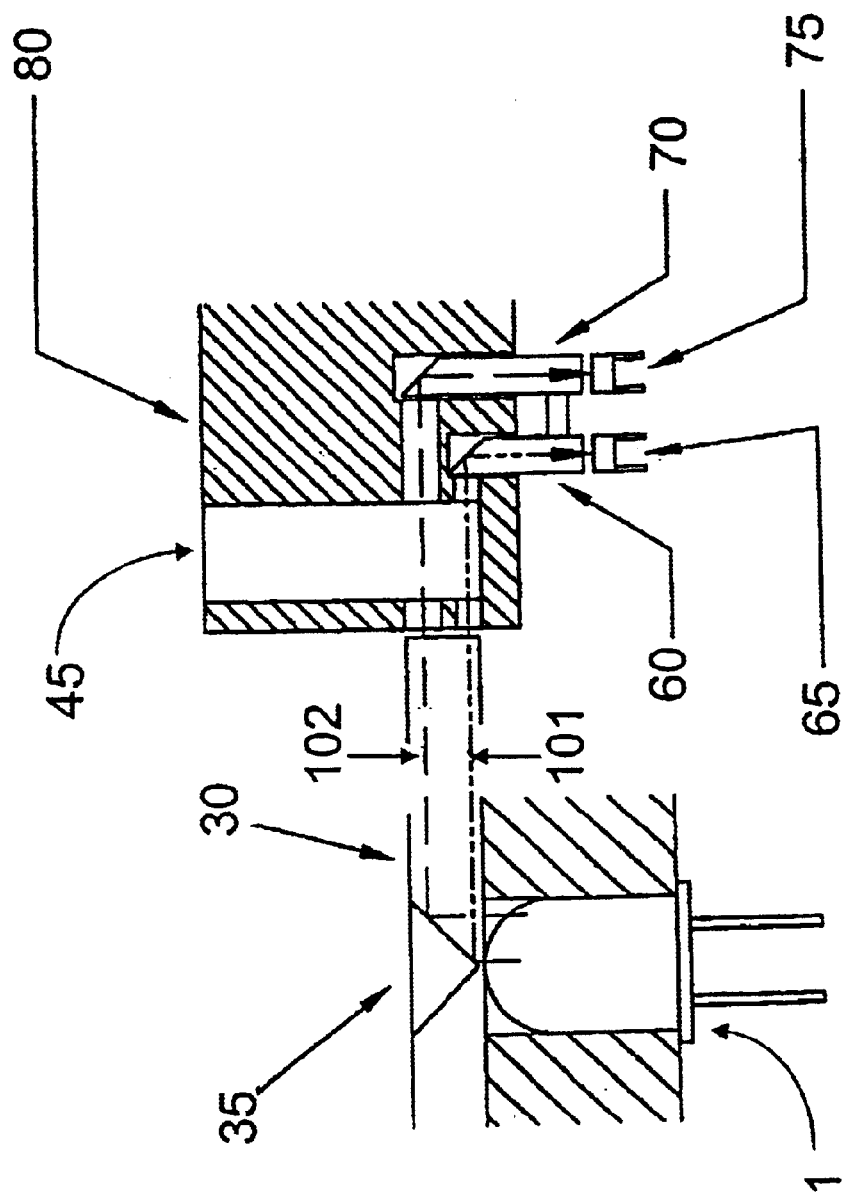

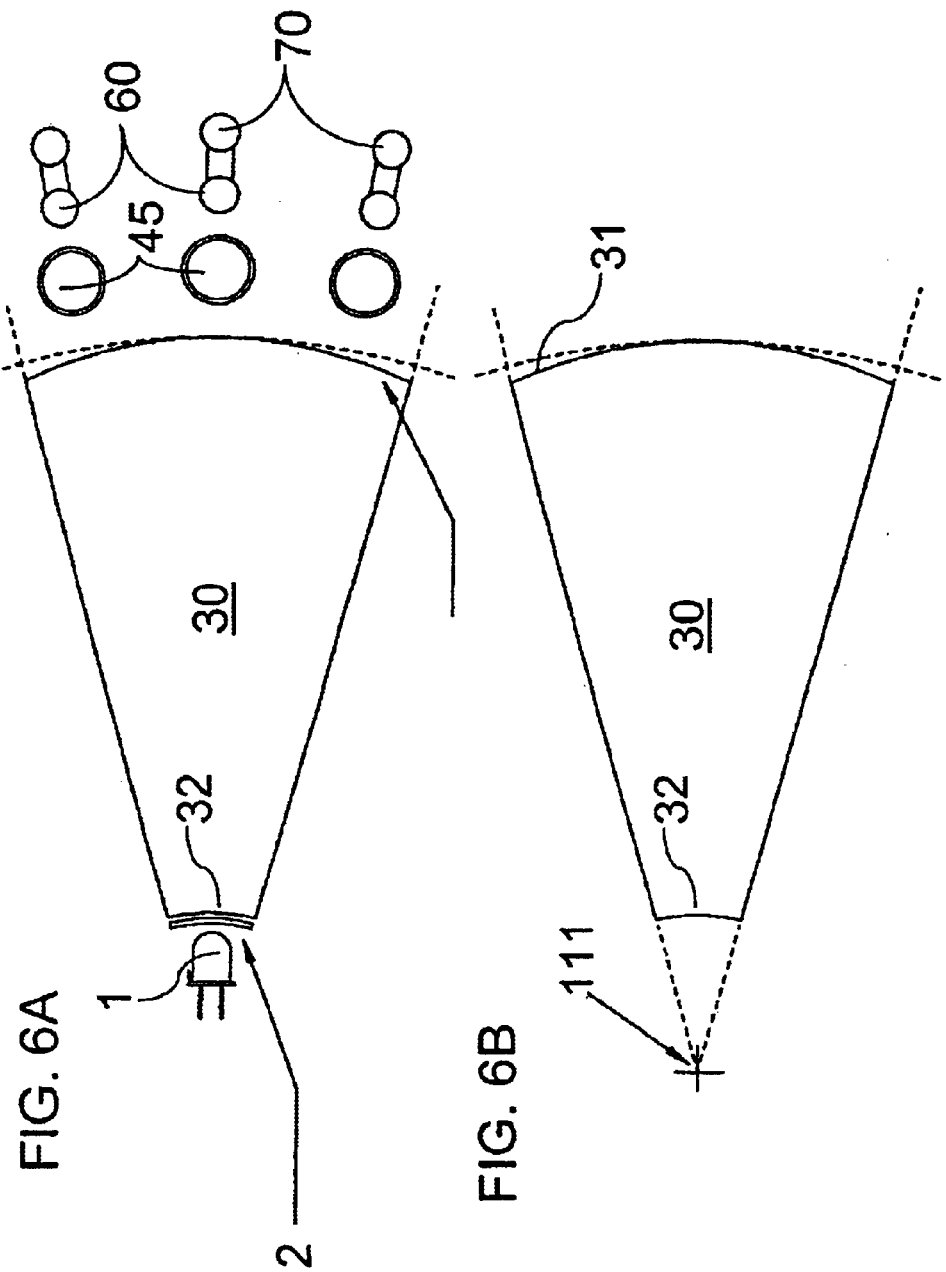

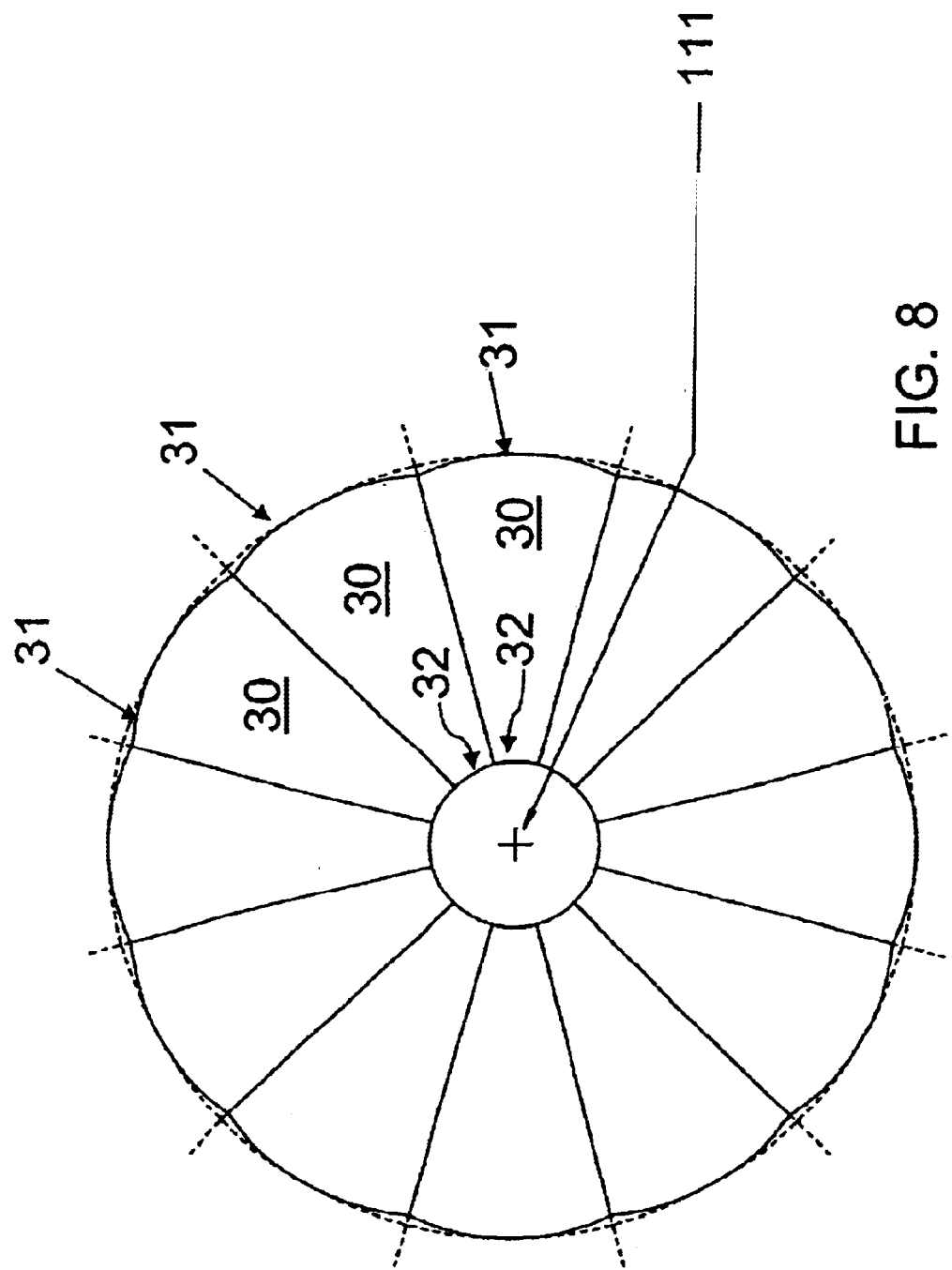

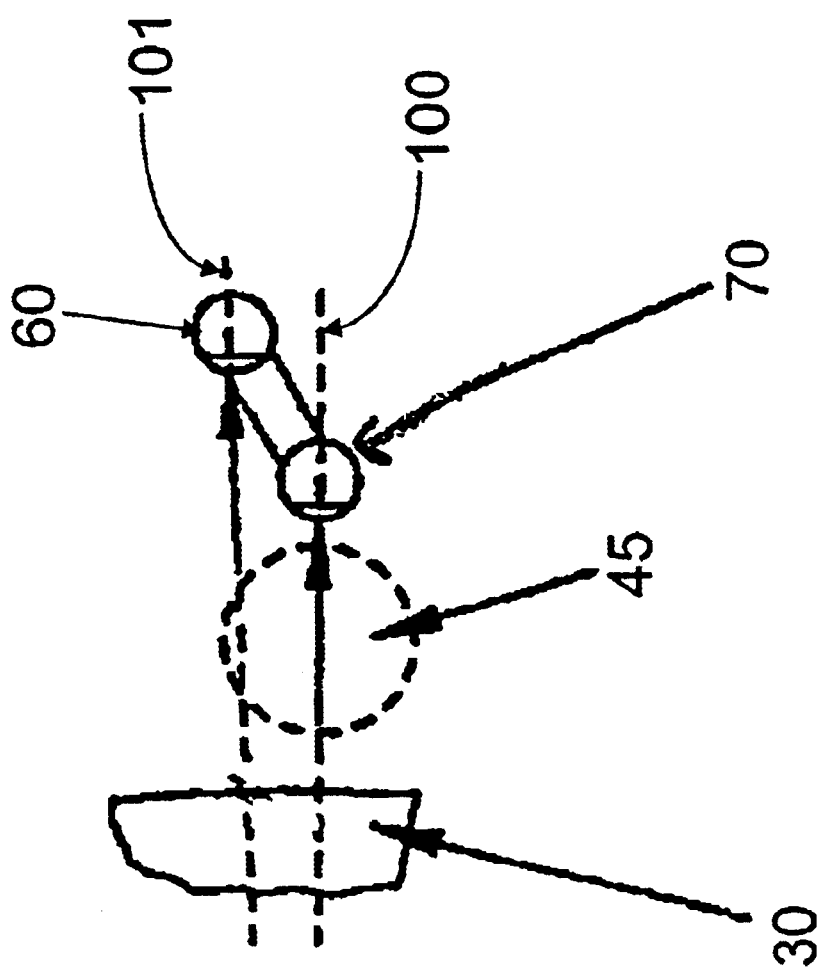

READER FOR CONDUCTING ASSAYS

CROSS-REFERENCE TO RELATED APPLICATIONS

This application claims the benefit of U.S. provisional application No. 60/167,618 filed Nov. 26, 1999.

BACKGROUND OF THE INVENTION

1. Field of the Invention

This invention is directed towards the Pyros Kinetix reader for conducting assays. More specifically, this invention is directed to providing an analytical device that, in one embodiment, conveniently and accurately assays both turbidity and chromogenic reactions in plural vessels.

2. Discussion of the Background

Optical techniques are commonly used to transduce a number of different chemical and biological parameters. Among many thousand such examples, turbidometric measurements can be used to bioassay and/or bioscreen for the presence of endotoxin using *Limulus* amebocyte lysate (LAL) such as PYROTELL-T (Associates of Cape Cod, Falmouth, Mass.). Similarly, chromogenic measurements can be used to bioassay and/or bioscreen for the presence of endotoxin using the POLYCHROME chromogenic formulation of LAL (Associates of Cape Cod, Falmouth, Mass.), which releases a yellow chromophore when exposed to endotoxin.

Many different instruments have been described that use optical techniques to transduce these and other such biological parameters. For example, Hoyt (U.S. Pat. No. 4,936,682) describes an instrument for measuring the light absorption characteristics of a plurality of samples arranged in a substantially circular pattern about a single incandescent light source. Incandescent light sources are however only suitable for performing certain types of assays since their emission intensity is primarily in the IR and long wavelength portion of the visible spectrum. Moreover, incandescent light sources require intensity adjustments to maintain a relatively constant emission flux, have limited operational lifetimes, and, as a consequence of resistive heating of the filament, dissipate large amounts of heat that often complicate temperature control in incubators. Finally, since incandescent sources require relatively large amounts of power, they are commonly driven by high power AC sources such as line sources and microcontroller-based modulation of incandescent source intensity is relatively difficult to implement. Shirasawa (U.S. Pat. No. 5,337,139) describes a multichannel optical measuring system which uses multiple branches of a quartz optical fiber to project light from mercury or xenon lamps at glass cuvettes that contain biological cell samples in order to perform fluorometric measurements. Shirasawa (U.S. Pat. No. 5,337,139) also describes that a light emitting diode (LED)/photodiode pair can be associated with each glass cuvette to generate a signal related to the intensity of transmitted light through the cuvette. Mioduski (U.S. Pat. No. 3,882,318) describes a reaction block configured to hold a reaction chamber where a specimen and a test reagent are mixed. The reaction block has two optical paths therethrough, one for conducting a transmittance measurement of the specimen/test reagent mixture, and the other to detect the presence of a reaction chamber within the block. Each reaction block has an associated printed circuit board for detecting light output from both paths. Noeller (U.S. Pat. No. 4,784,947) describes a method for photographically recording fluorometric and nephelometric analyses performed using a photo-flash or a strobe light photon source. As both the light transduction and light generation described by Noeller (U.S. Pat. No. 4,784,947) only occurs at discrete times, continuous monitoring and automated data analysis is not possible.

The disclosure of each of the above-noted patents is incorporated herein by reference.

SUMMARY OF THE INVENTION

Accordingly, one object of this invention is to provide a novel method and device for conducting assays.

Another object of this invention is to provide a novel method and device that, in one embodiment, allows a user to simultaneously assay both turbidity and chromogenic reactions in plural vessels.

Another object of this invention is to provide a novel method and device that, in one embodiment, allows a user to conduct several assays simultaneously, each assay not necessarily having a same start time.

Another object of this invention is to provide a novel method and device that, in one embodiment, reduces device component and assembly costs, minimizes the size of the device, makes repair easier.

Another object of this invention is to provide a novel method and device that, in one embodiment, allows a user to incubate plural assays in plural vessels using a minimum of power while maintaining a desired incubation temperature.

These and other objects of the invention can be realized by using a PYROS KINETIX READER and similar devices. Such devices can include, according to one embodiment, a single LED source providing illumination to plural vessels through a radial waveguide. Some embodiments can include two LED sources in a single device, each illuminating plural vessels along a different radial waveguide. Some embodiments can include more than two LED sources in a single device. Other embodiments can include one or more radial waveguides for presenting emitted light to the plural vessels at a high intensity. Other embodiments can present emitted light along two radial waveguides through a single vessel, the first radial waveguide being used to detect a presence of the vessel and the second radial waveguide being used to transduce an optical property of an analyte within the vessel. Some embodiments include modulation of the emission intensity of the one or more LED sources, this modulation being, e.g., a step function. In some embodiments, this modulation is microprocessor-based. In other embodiments, this modulation is mechanical, analog, or otherwise electronically implemented. In some embodiments, the LED source(s) emit substantially at 470 nm +/−30 nm. In some embodiments, one or more optical filters is placed along an optical path that passes through the vessel.

Other embodiments of such devices can include the vessels arranged in a substantially circular geometry around the LED light source(s). Other embodiments may include plural groups of two or more vessels at two or more different radii about a center. Another embodiment may include two groups of 48 vessels at two different radii about the center. In some embodiments, an LED is positioned at the center point. In some embodiments, one or more optical waveguides is used to substantially evenly distribute light from one or more LED's to several vessels. In some embodiments, a lens is used to position a virtual image of one or more LED's at the center. In some embodiments, multiple LED's are vertically staggered along a line passing through the center.

Other embodiments of such devices can include a single printed circuit board containing plural phototransducers.

Some embodiments may include a single printed board having all phototransducers. Some embodiments provide plural vessels in a same plane, and a plane of such a single printed circuit board being substantially parallel to such a plane. Some embodiments provide a plane of such a single printed circuit board below at least one vessel. In some embodiments, a light pipe is used to guide light transmitted along an optical path through a vessel to such a single printed circuit board.

Other embodiments of such devices can include a multi-component support for the vessels, a first component being chosen to conduct heat for incubating one or more vessels at a set temperature. In some embodiments, another component is chosen to thermally insulate the first component and reduce power demands of the device. In some embodiments, the other component is lighter that the first component and reduces the net weight of the device.

Other embodiments of such devices can include a precalibrated temperature transducer that reduces calibration demands for operating such a device.

The aforementioned and other objects of the invention can also be realized using methods that are simple to implement upon the PYROS KINETIX READER and other similar devices. A method for performing assays can involve generating light using a LED, radially guiding a portion of the generated light, transmitting a portion of the guided light through a plurality of vessels, and transducing a portion of the transmitted light to assay a sample. In some embodiments, a portion of the generated light can be transmitted through a side or a bottom portion of the plurality of vessels and used to detect the presence of the plurality of vessels. In other embodiments, a portion of the transmitted light can be reflected using a light pipe. In some embodiments, a portion of the generated light can be diverged. In other embodiments, the generated light can be modulated to yield a background measurement.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIGS. 1A and 1B illustrate, respectively, a top view and a side view of an exemplary optical system according to the present invention;

FIGS. 2A, 2B, and 2C illustrate a side view of various light paths through an exemplary optical system without a sample holding vessel present, with a sample holding vessel present, and with a sample holding vessel present at an increased magnification;

FIGS. 6A and 6B illustrate, respectively, a top view and a side view of a third exemplary embodiment of the radial light guide 30;

FIG. 8 illustrates a schematic of a top view of an exemplary arrangement of a optical system that includes the third exemplary embodiment of the radial light guide 30;

FIGS. 13A–C illustrate a top view in the absence of an analyte holding vessel 40, a top view in the presence of an analyte holding vessel 40, and a side view in the presence of an analyte holding vessel 40 that uses an exemplary side wall tube detection scheme with a single radial light guide 30;

DETAILED DESCRIPTION OF THE PREFERRED EMBODIMENTS

Figure 2C:
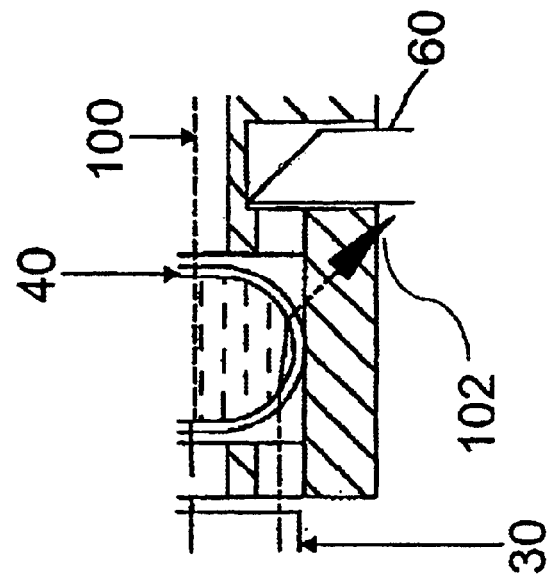

Referring now to the drawings, wherein like reference numerals designate identical or corresponding parts throughout the several views, and more particularly to FIG. 1 thereof, which illustrates an exemplary optical system according to the present invention. The illustrated optical system generates light, radially guides it to one or more vessels containing an analyte, transmits the light through the vessel and/or the analyte, and then pipes the light to one or more light transducers where it is transduced. As used herein, radial guiding refers to the transmission of light to plural vessels along plural optical paths, wherein the transmittance along the various paths is substantially equal. This situation is possible to implement using a circular (or arcular) waveguide with a source located at the center, hence giving rise to the term "radial guiding."

In FIGS. 1A and 1B, LED source 1 generates and emits photons, and can also optionally serve to collimate and/or focus the generated photons. Examples of commercially available LED's that can form the LED source 1 are the Nichia P/N NSPB500S, the Kingbright P/N L934MBC, and the Hewlett-Packard P/N HLMP-CB16. LED's generate relatively large photon fluxes over relatively narrow bandwidths, especially relative to incandescent sources which emit over a very large bandwidth. In one embodiment, LED source 1 can generate photons centered around substantially 470 nm with a bandwidth +/−30 nm, although those skilled in the art can increase or decrease the center wavelength and the bandwidth surrounding it to provide different responses. Naturally, plural LED's may be used along with multiple versions of the illustrated optical system in the same assay device. In such a case, LED's with different center wavelengths and/or intensities may be selected to, e.g., provide broader dynamic range for assays, allow dual wavelength assays to, e.g., increase sensitivity and/or allow a user to use plural chromophores and/or obtain better background correction information.

Also illustrated in FIG. 1B is an optical filter 2 between the LED source 1 and the radial waveguide 30. The filter 2 is optional; since a LED emission spectrum is already relatively narrowband, it is often not necessary to include filter 2, which further lowers the cost and power requirements of the optical system. However, in some applications that have precise wavelength requirements, such as spectroscopic analyses or chromogenic assays of complex samples, a filter 2 may be desirable.

In the illustrated embodiment, light emitted by LED source 1 is guided radially by a radial light guide 30 that includes a light coupling total internal reflection (TIR) cone 35 for coupling the emitted light into the radial light guide 30. As illustrated, light coupling TIR cone 35 is centered within the radial light guide 30 and substantially above the LED source 1. In such a geometry, light emitted by LED source 1 is substantially evenly transmitted from the center of light guide 20 toward the perimeter of radial light guide 30. Radial light guide 30 can be formed of, e.g., acrylic cast into a mold that forms light coupling TIR cone 35. The radial light guide 30 with a light coupling TIR cone 35 allows a 20 to 100 mW LED source 1 to provide as much illumination to the analyte holding vessel 40 as a 20 W incandescent bulb.

A single well 45 configured to support an analyte holding vessel 40 is illustrated beyond the perimeter of the radial light guide 30. Naturally, it is both possible and desirable to use plural wells 45 and analyte holding vessels 40 (not shown). The distribution of such wells 45 relative to the radial light guide 30 will be discussed further in, e.g., FIGS. 3 and 11. The illustrated well 45 is configured to support an analyte holding vessel 40 that is a test tube, although other suitable vessels, such a optical cuvettes and capillaries, may be used. It is only important that analyte holding vessel 40 be sufficiently transparent over the emission spectrum of LED source 1 to perform the desired assay.

The exemplary optical system of FIG. 2 also includes a pair of light pipes 60 and 70 along a pair of paths that join the real or virtual position of the LED source 1 and some point in or on an analyte holding vessel 40 in the well 45. The pair of light pipes 60 and 70 neighbor the well 45. Light transmitted through the well 45 is incident upon the pair of light pipes 60 and 70 (provided no analyte holding vessel 40 is present), and reflected in a direction determined by the orientation of a total internal reflection (TIR) surface 21. The pair of light pipes 60 and 70 thus allow an optical transducer to be located away from a straight line path that join the real or virtual position of the LED source 1 and some point in or on the analyte holding vessel 40 in the well 45. This is desirable in the interest of simplifying device design, limiting the number of harness connections, decreasing the cost of the device, and simplifying maintenance and repair. As illustrated, the light receiving portion of light pipe 60 is located along a path that joins the real or virtual position of the LED source 1 and a point on the bottom curvature of an analyte holding vessel 40 positioned in the well 45. When an analyte holding vessel 40 is present in well 45, light passing along this line through the radial light guide 30 is significantly deflected out of this path due to refraction by the analyte holding vessel 40, and a light transducer 65 located at the output of light pipe 60 can easily detect the insertion and/or removal of analyte holding vessel 40 by monitoring the intensity of the received light. Absorption and/or reflection of the light that passes along this path can also decrease the intensity of the received light and detect the presence of an analyte holding vessel 40 in well 45. Alternatively, the light receiving portion of light pipe 60 can be located along a path that joins the real or virtual position of the LED source 1 and a point on the side curvature of the analyte holding vessel 40 to obtain a similar sensitivity, as further illustrated in FIGS. 13A–C.

Light pipe 70, on the other hand, is preferably located along a light path that joins the real or virtual position of the LED source 1 and a point near the center of an inserted analyte holding vessel 40, but away from the bottom. As such, a relatively long pathlength through the analyte holding vessel 40 is examined and refraction (due to, e.g., tubular analyte holding vessels 40) is minimized.

In the illustrated embodiment of FIG. 1B, both light pipes 60 and 70 receive light 20, from a same radial light guide 30. This is not necessarily the case. For example, two different radial light guides 20 can each transmit light to a single respective light pipe 60 and 70. Moreover, in the case of plural test wavelengths, even three or more different radial light guides 20 can be used with associated light pipes.

In the illustrated embodiment, both TIR surfaces 21 reflect light downward, substantially at right angles relative to the respective path of that light through the analyte holding vessel 40. This is preferred, since no tilting and/or stoppering of the analyte holding vessel 40 is required and the light transducers 65 and 75 for multiple analyte holding vessels 40 can be positioned in a single printed circuit board located below and substantially parallel with the radial light guide 30. Naturally, in some embodiments of the invention, the TIR surfaces 21 and pair of light pipes 60 and 70 can be eliminated in whole or in part, although this will often require the placement of the light transducers 65 and 75 for multiple analyte holding vessels 40 upon multiple printed circuit boards. At the output of the pair of light pipes 60 and 70, a pair of light transducers 65 and 75 can be used to determine the transmissivity of both optical paths. Suitable, commercially available light transducers 65 and 75 include photodiodes such as the Centrovision P/N BPW-34, Hamamatsu P/N S4707-01, Hamamatsu P/N S3407-01, UDT Sensors P/N BPW34, UDT Sensors P/N BPW34B, Infinion P/N BPW34, Infinion P/N BPW34 B, and the Perkin Elmer P/N VTD34.

Figure 2B:
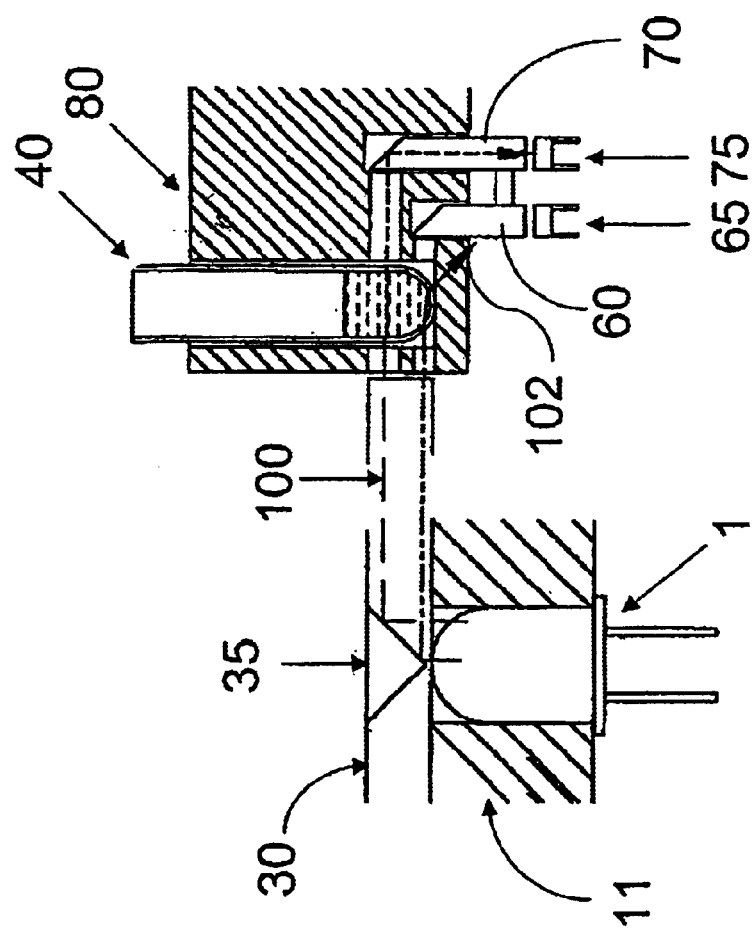

A further illustration of side views of various light paths 100, 101, and 102 through an exemplary optical system with and without a sample holding vessel present is provided in FIGS. 2A, 2B, and 2C (albeit at higher magnification). In FIG. 2A, photons generated at the LED source 1 are reflected by the light coupling TIR cone 35 and carried along radial light guide 30 to a vessel support 80 that may or may not support an analyte holding vessel 40 therein. If an analyte holding vessel 40 is not supported by the a particular well 45 of the vessel support 80, then the light path 101 will conduct a relatively high intensity of light to light pipe 60, which in turn conducts the light to light transducer 65. On the other hand, if a (filled) analyte holding vessel 40 is supported by a particular well 45 of the vessel support 80, then light originally on light path 101 is deflected along light path 102, and a relatively low intensity of light is received at light pipe 60 and light transducer 65. Thus, by measuring an intensity of the light received at light transducer 65, the presence of an analyte holding 9 vessel 40 in a well 45 of the vessel support 80 can be made.

FIG. 2C illustrates a side view of various light paths through an exemplary optical system with a sample holding vessel present at an increased magnification. As illustrated, light that has passed through the radial light guide 30 is directed downward due to refraction caused by the base of an analyte holding vessel 40 in a well 45 of the vessel support 80. Refraction need not be the physical origin of the decreased light intensity received at light guide 60. For example, reflection and/or absorption can also cause reduced light transmission to light guide 60.

As illustrated in FIGS. 2A, 2B, and 2C, since light path 100 is incident upon a position substantially at the middle of analyte holding vessel 40, the direction of light path 100 remains substantially unchanged by the presence of analyte holding vessel 40. Naturally, the intensity of light transmitted along light path 100 will change, and this intensity change will be used to assay the contents of analyte holding vessel 40.

Also illustrated in FIGS. 2A and 2B is a positioning sleeve 11 arranged about the LED source 1. The positioning sleeve 11 serves to accurately center LED source 1 directly under light coupling TIR cone 35, ensuring substantially uniform radial illumination by light guided through radial light guide 30.

Figure 3A:
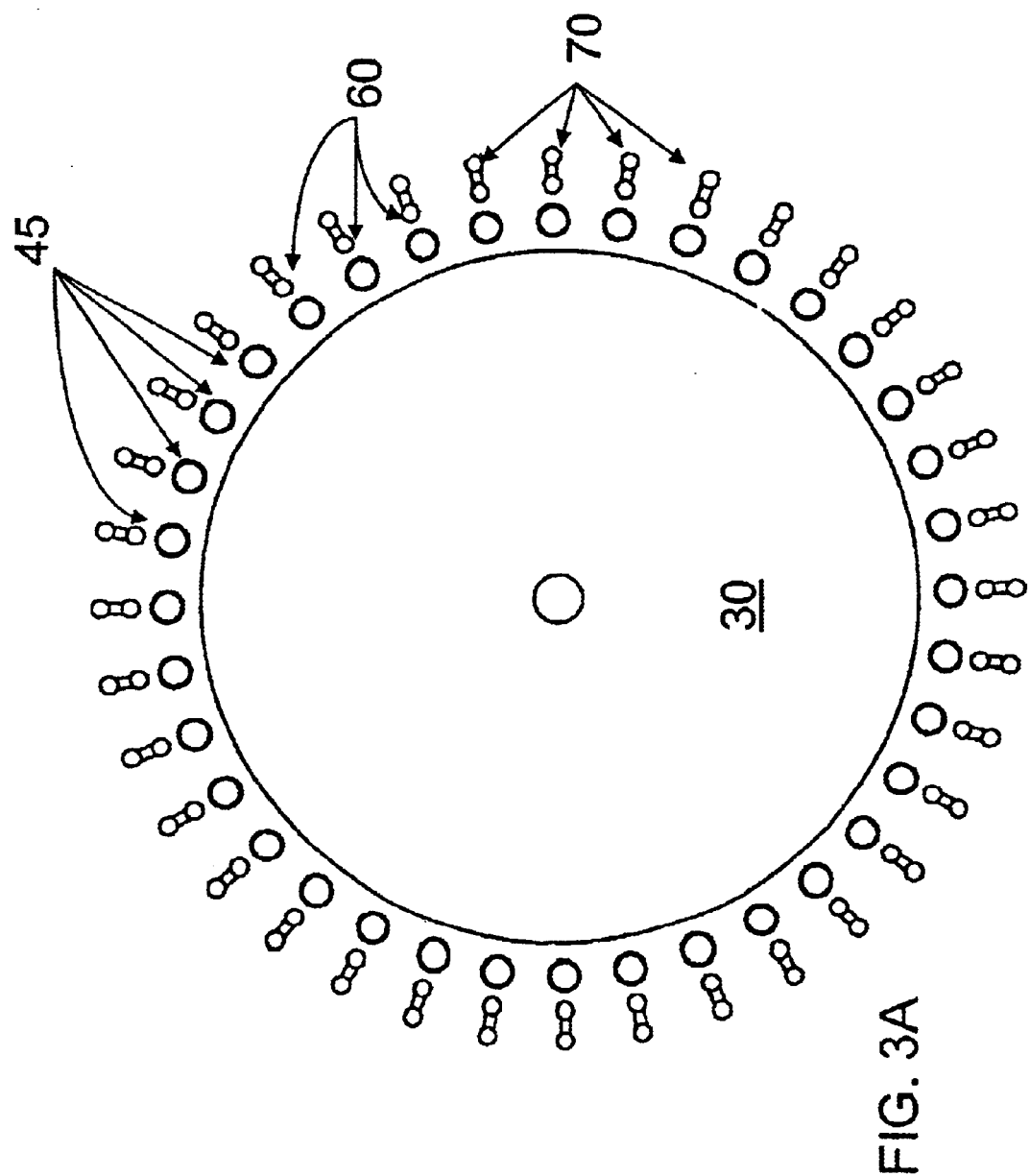
FIGS. 3A and 3B illustrate, respectively, a top view and a side view of an exemplary embodiment of the optical system that includes a central light source with multiple wells.
Figure 3B:
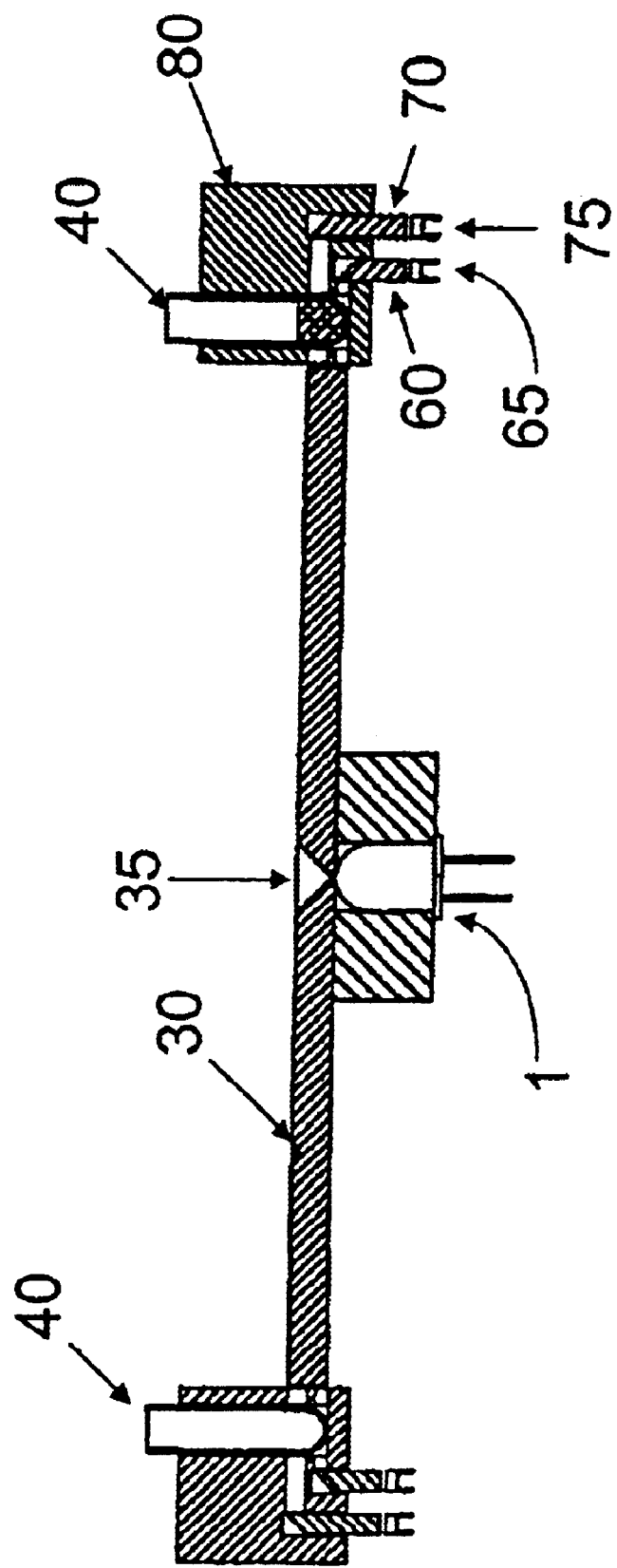

FIGS. 3A and 3B illustrate, respectively, a top view and a side view of an exemplary embodiment of the optical system that includes a central light source with multiple wells 45 of the vessel support 80 for holding multiple analyte holding vessels 40. In the illustrated embodiment, the multiple wells 45 are arranged radially about the light coupling TIR cone 35 of the radial light guide 30. As such, the multiple wells 45 of the vessel support 80 receive substantially equal radiant fluxes from the LED source 1. Moreover, if the vessel support 80 is radially symmetric, this radial symmetry can be exploited to maintain all wells 45 of the vessel support 80 at a substantially equal temperature. For example, if the vessel support 80 includes a ring made of a thermally conducting material (e.g., a metal such as aluminum or copper such as heat conducting block 85 shown in e.g., FIG. 10), then a heater ring (such as heater 90 shown in e.g., FIG. 10) can be disposed just inside and/or outside of the vessel support 80 and all wells 45 of the vessel support 80 will be maintained at a substantially equal temperature. Thus, even if the absolute incubation temperature is subject to errors due to, e.g., thermal fluctuations and/or miscalibrated equipment, then accurate differential measurements across samples within different wells 45 of the vessel support 80 will still be possible. Both the heating of and disposition of wells 45 within the vessel support 80 will be discussed in more detail in regard to FIG. 9.

Figure 4A:
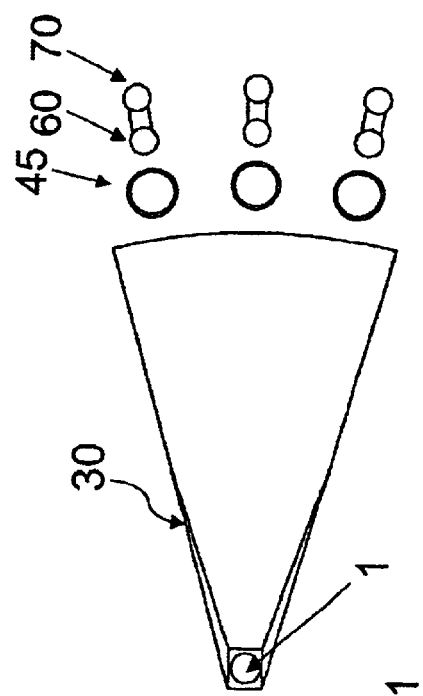
FIGS. 4A and 4B illustrate, respectively, a top view and a side view of a second exemplary embodiment of the radial light guide 30.
Figure 4B:
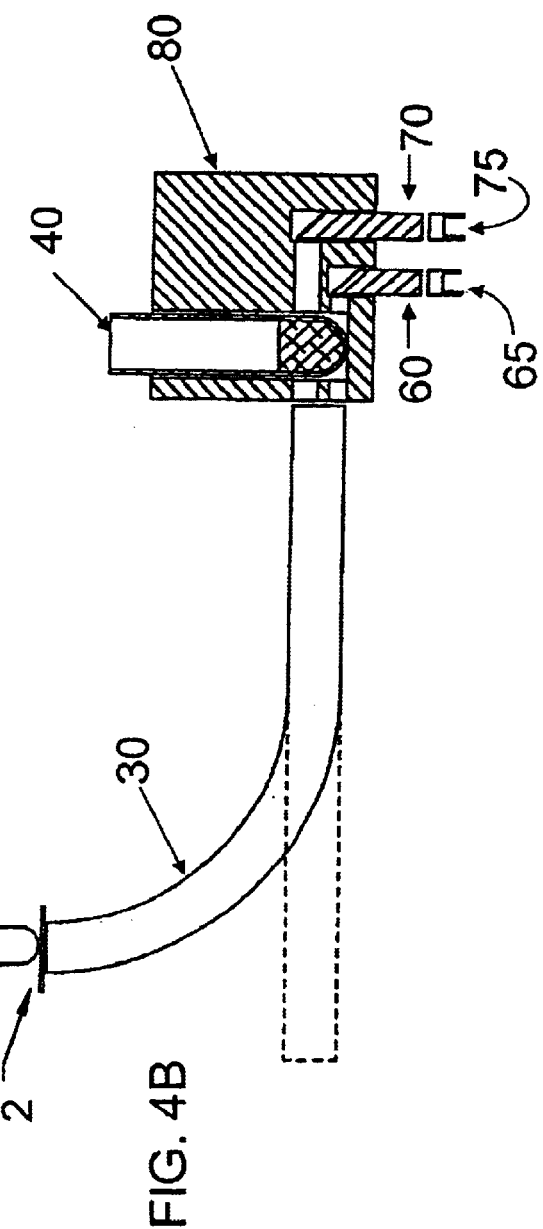

FIGS. 4A and 4B illustrate, respectively, a top view and a side view of a second exemplary embodiment of the radial light guide 30, namely a curved wedge lightguide. As with the radial light guide 30 of FIGS. 1A and 1B, the radial light guide 30 of FIGS. 4A and 4B guides light emitted by LED source 1 (optionally passing through a light filter 2) radially to multiple wells 45 within the vessel support 80. With curved wedge waveguides, plural LED sources can be vertically staggered, and the light illuminating the analyte holding vessels 40 in wells 45 appear to originate from a single, central source 111. The radial light guide 30 of FIGS. 4A and 4B is particularly useful for several different reasons. For example, by reducing the total number of wells 45 that are illuminated by a particular LED source 1, then the intensity per well 45 is increased. This effect can be augmented by collecting and/or focusing light upon the end of radial light guide 30 using, e.g., lenses and spherical and/or parabolic reflectors (not shown). The increased light intensity per well 45 is particularly useful when, e.g., assaying samples with a low transmittance. Another reason that the radial light guide 30 of FIGS. 4A and 4B is particularly useful is that several such light guides and LED sources 1 may be used in a single device for conducting assays. This broadens the range of available assays that may be performed upon the analyte holding vessels 40 in vessel support 80. For example, some wells 45 of the vessel support 80 may be dedicated to assaying for one chromophore, while other wells 45 may be dedicated to assaying for another chromophore that has a different absorption spectrum. Since different LED sources 1 can be used to sample separate groups of wells 45, each chromophore can be probed at a wavelength for which it has a near-maximum response (e.g., absorbance), and an increased sensitivity to each chromophore can be achieved. Moreover, different filters can be inserted between each of the LED sources 1 and the radial light guides 30.

Figure 5A:
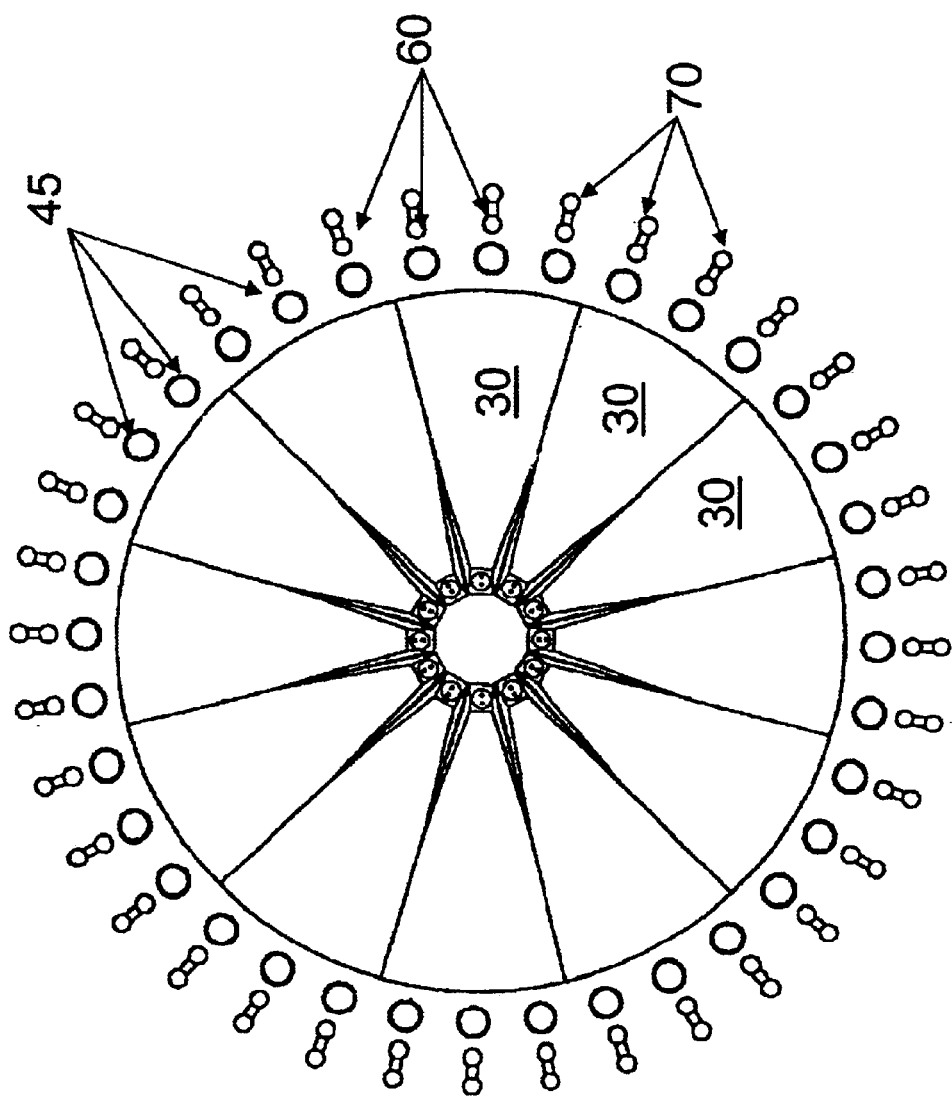
FIGS. 5A and 5B illustrate, respectively, a top view and a side view of an exemplary embodiment of the optical system that includes the second exemplary embodiment of the radial light guide 30.
Figure 5B:
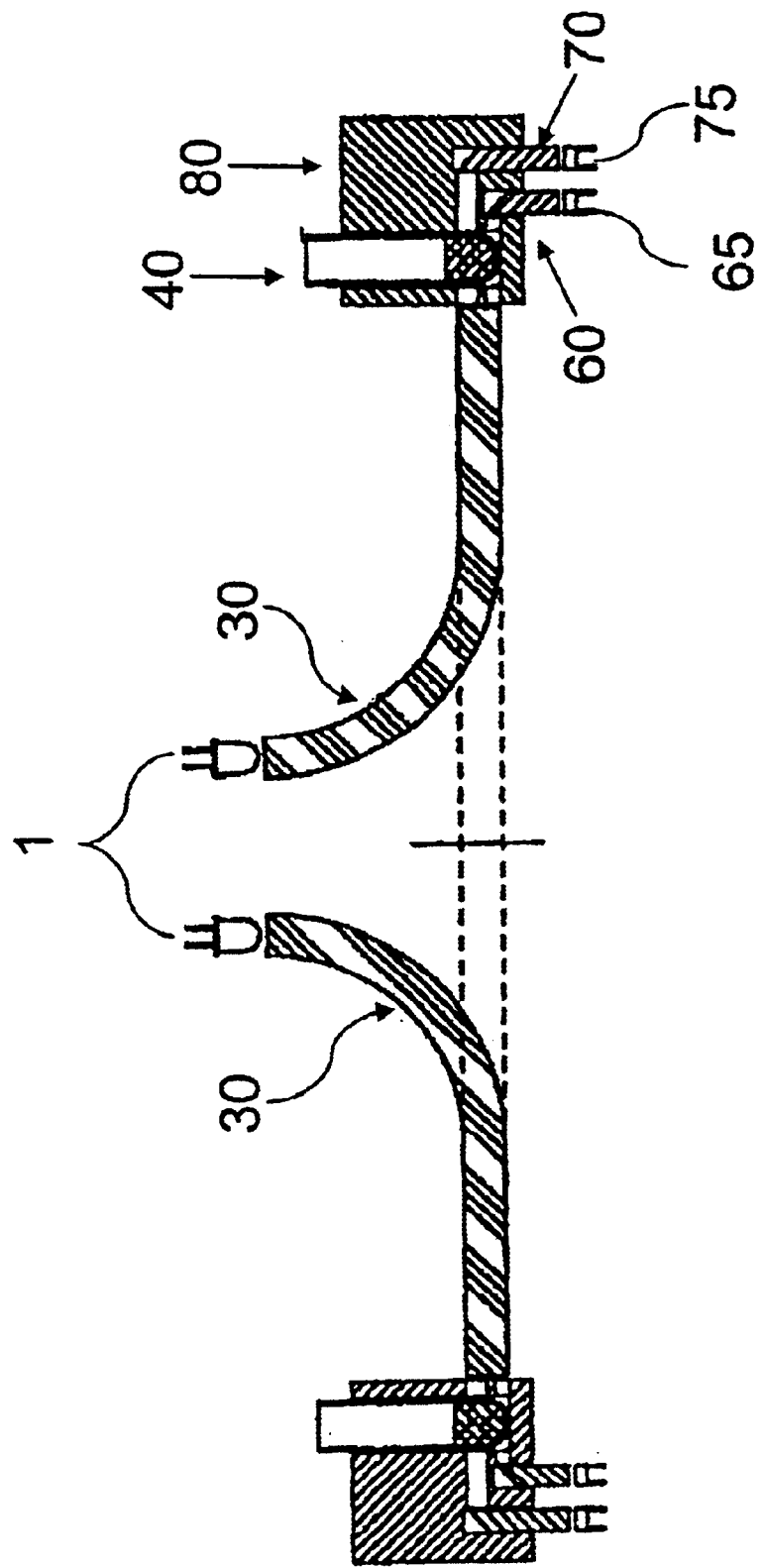

FIGS. 5A and 5B illustrate, respectively, a top view and a side view of an exemplary embodiment of the optical system that includes the second exemplary embodiment of the radial light guide 30. Plural LED sources 1 are available in this optical system, and light emitted by these LED sources 1 is substantially evenly distributed along the perimeter of radial light guide 30 due to the symmetric arrangement of plural versions of the second exemplary embodiment of the radial light guide 30 about a central axis. As described before, the plural LED sources 1 can have similar or different emission spectra, as desired.

FIGS. 6A and 6B illustrate, respectively, a top view and a side view of a third exemplary embodiment of the radial light guide 30, namely a lensmatic wedge lightguide. As with the radial light guide 30 of FIGS. 1A and 1B, the radial light guide 30 of FIGS. 6A and 6B guides light emitted by LED source 1 (optionally passing through a light filter 2) radially to multiple wells 45 within the vessel support 80. However, the lensmatic wedge lightguide has at least one of the light coupling face 32 (where light is received from the LED source 1) and a light decoupling face 31 (where light is transmitted to the analyte holding vessels 40 in wells 45) with a radius of curvature that is smaller than the radius of the one or more concentric rows of wells 45 in the vessel support 80 for the analyte holding vessels 40. The lensmatic wedge lightguide version of the radial light guide 30 thus can be designed to create a virtual image 11 of the LED source 1 directly at the center point of the radius of one or more concentric rows of wells 45 in the vessel support 80. Once again, substantially even radial distribution of light emitted by plural LED sources 1 can be assured, even though these sources do not occupy the same physical space.

The third embodiment (lensmatic wedge) radial light guide 30 of FIGS. 6A and 6B is particularly useful for reasons similar to those described in regard to the second embodiment (curved wedge) of the radial light guide 30 of FIGS. 4A and 4B. For example, by reducing the total number of analyte holding vessels 40 that are illuminated by a particular LED source 1, then the intensity per analyte holding vessel 40 is increased. This effect can be augmented by collecting and/or focusing light upon the end of radial light guide 30 using, e.g., lenses and spherical and/or parabolic reflectors (not shown). The increased light intensity per analyte holding vessel 40 is particularly useful when, e.g., assaying samples with a low transmittance. Another reason that the third embodiment (lensmatic wedge) radial light guide 30 of FIGS. 6A and 6B is particularly useful is that several such lightguides and LED sources 1 may be used in a single device for conducting assays. This broadens the range of available assays that may be performed upon the analyte holding vessels 40 in vessel support 80. For example, some wells 45 of the vessel support 80 may be dedicated to assaying for one chromophore, while other wells 45 may be dedicated to assaying for another chromophore that has a different absorption spectrum. Since different LED sources 1 can be used to sample separate groups of wells 45, each chromophore can be probed at a wavelength for which it has a maximum absorbance, and an increased sensitivity to each chromophore can be achieved. Moreover, different filters can be inserted between each of the LED sources 1 and the radial light guides 30.

In contrast with the second embodiment (curved wedge) radial light guide 30 of FIGS. 4A and 4B, multiple copies of the third embodiment (lensmatic wedge) radial light guides 20 of FIGS. 6A and 6B can be maintained in a substantially single plane. As such, it is easier to stack multiple layers of the third embodiment (lensmatic wedge) radial light guides 20 so that each well 45 in vessel support 80 can be assayed by a user-selected wavelength independent of the location of well 45. A single well 45 may also be assayed at multiple wavelengths using this approach by, e.g, multiplexing the transmission wavelength through a single well 45 by shifting the phase of an on/off modulation for different LED sources 1 stacked atop one another but illuminating a single well 45. The stacking of multiple layers of the third embodiment (lensmatic wedge) radial light guides 20 can be accompanied by the addition of further light pipe(s) and transducer(s) (sensitive to the wavelength(s) of the further LED sources 1) so that complete additional, independent, optical channels can be formed. Finally, lensmatic wedge radial light guides 20 are relatively easy to make.

Figure 7A:
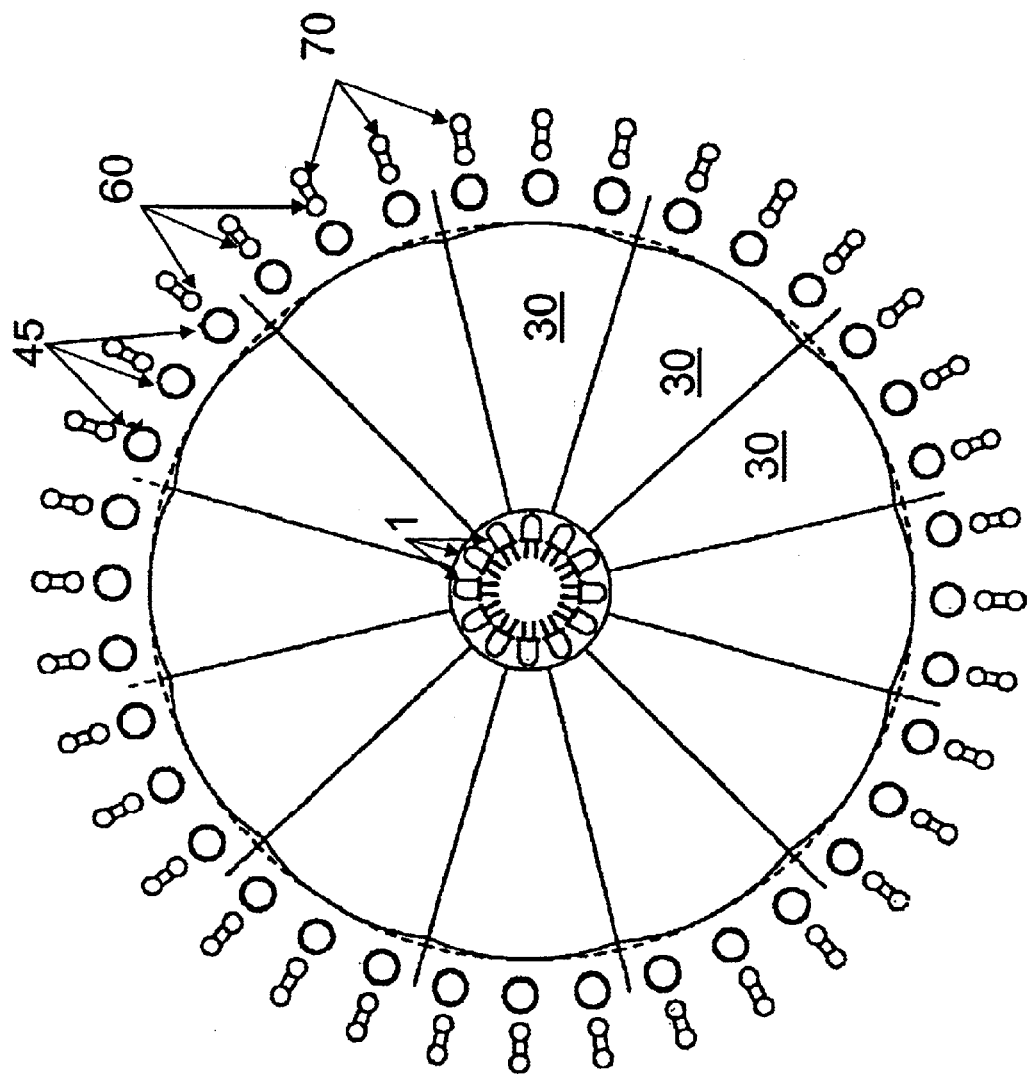
FIGS. 7A and 7B illustrate, respectively, a top view and a side view of an exemplary embodiment of the optical system that includes the third exemplary embodiment of the radial light guide 30.
Figure 7B:
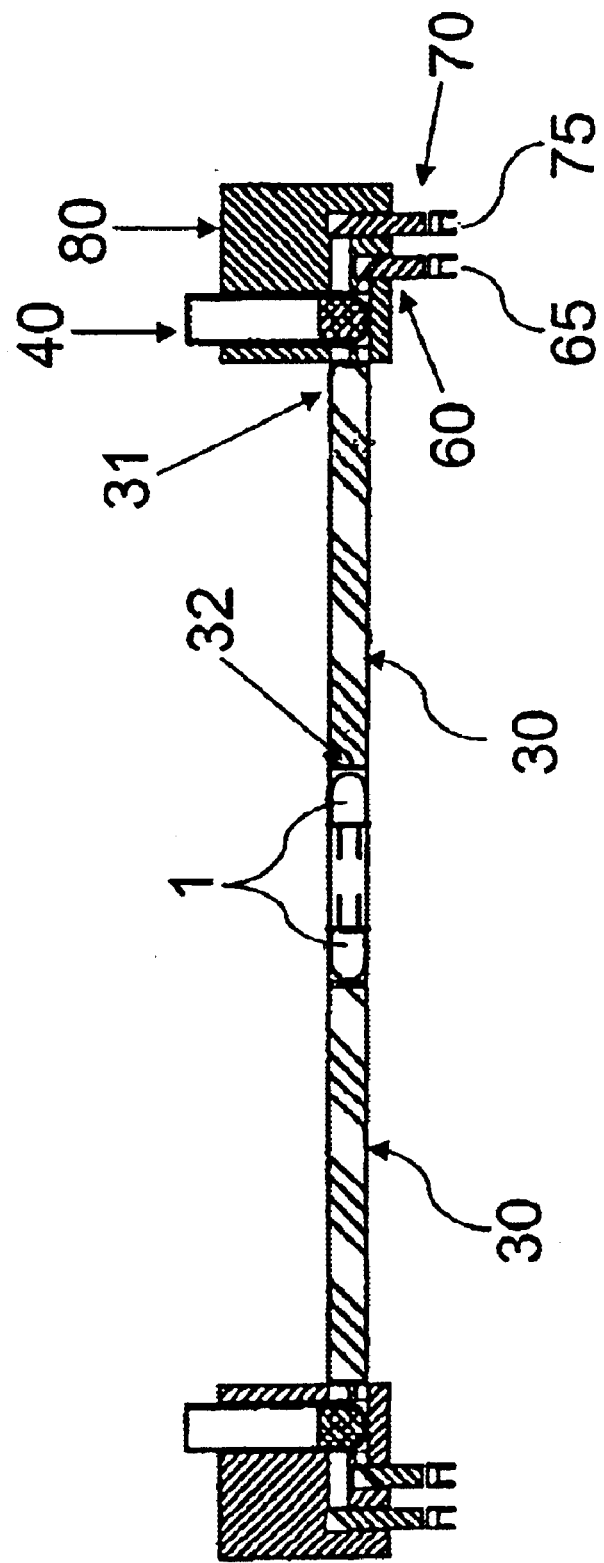

FIGS. 7A and 7B illustrate, respectively, a top view and a side view of an exemplary embodiment of an optical system that includes the third exemplary embodiment of the radial light guide 30, namely the lensmatic wedge. Similarly to FIGS. 5A and 5B, plural LED sources 1 are available in this optical system, and light emitted by these LED sources 1 is substantially evenly distributed along the perimeter of radial light guide 30 due to the symmetric arrangement of plural versions of the third exemplary embodiment of the radial light guide 30 about a central axis. As described before, the plural LED sources 1 can have similar or different emission spectra, as desired.

FIG. 8 illustrates a schematic of a top view of an exemplary arrangement of a optical system that includes the third exemplary embodiment of the radial light guide 30, namely the lensmatic wedge. This is presented to emphasize that, in this case, all radial light guides 20 can form a virtual image 111 of a respective LED source 1 at a point central to all wells 45 of the vessel support 80.

Figure 9:
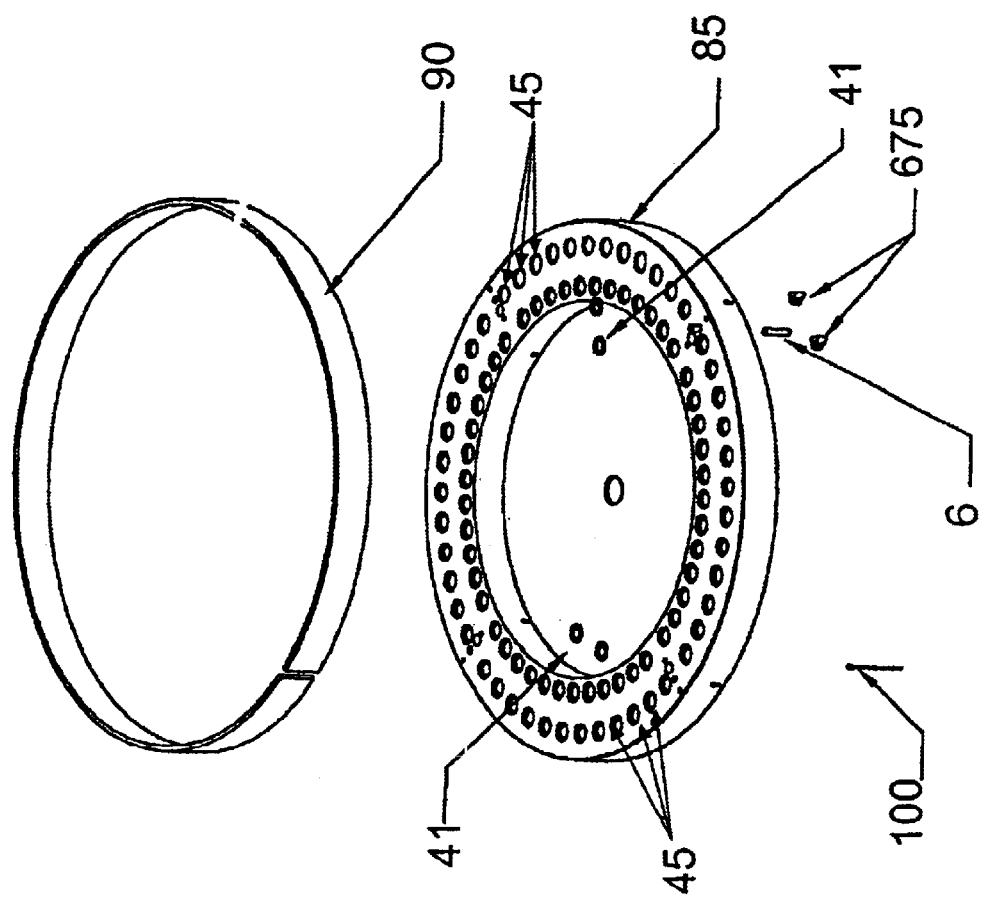
FIG. 9 illustrates an exemplary vessel support 80 containing two concentric circular rows of wells 45, as well as various components to be entirely or partially inserted into the exemplary vessel support 80.

FIG. 9 illustrates an exemplary heat conducting block 85 from a vessel support 80 that contains two concentric circular rows of wells 45. Also shown are a heater ring 90, a temperature transducing thermistor 1000, a fixing dowel pin 6, O-rings 41, and dual light pipes 675. The heat conducting block 85 contains two concentric circular rows of wells 45 configured to support an inserted analyte holding vessel 40 (not shown). By using two concentric circular rows of wells 45, the capacity of the instrument (i.e., number of wells 45) can be increased. This allows for the parallel assaying of multiple analyte holding vessels 40 without an unwieldy increase in the dimensions of the vessel support 80. In one embodiment, there are 96 wells 45 within a single vessel support 80, distributed in two concentric circular rows.

In the illustrated embodiment, the wells 45 are relatively deep and a significant portion of an inserted analyte holding vessel 40 can be enclosed within each well 45. Thus, cross bores (not shown) directed radially through the vessel support 80 are necessary to allow the transmission of light through the vessel support 80 to the wells 45 and light pipes 60 and 70.

The exemplary vessel support 80 also includes a heater ring 90 that surrounds the heat conducting block 85. By maintaining radial symmetry about a central axis for both the heater ring 90 and the wells 45 in the heat conducting block 85, a relatively equal temperature can be maintained at each well 45 in a single row. As such, even if absolute temperature control is ineffective, accurate differential measurements across analyte holding vessels 40 incubated in a same row can be made. In one embodiment, heater ring 90 is formed from a low power, DC heater. The power supply for such a heater ring 90 can be placed under microprocessor control and, given that the supply is DC, a source of AC electrical noise within the device for assays is eliminated.

The exemplary vessel support 80 also includes a temperature transducing thermistor 1000 that is favorably disposed in contact with or within the heat conducting block 85. The temperature transducing thermistor 1000 can be used to generate a control signal used for the closed loop control of the temperature of heat conducting block 85. A suitable, commercially available thermistor 1000 is the P/N QT06002-128 REV A from Quality Thermistor, Inc. For example, if the temperature transducing thermistor 1000 indicates that the temperature of the heat conducting block 85 has dropped below a predetermined (and possibly operator-set) temperature, then increased power can be presented to heater ring 90, and the temperature of the heat conducting block 85 increased. In some embodiments of the device, assay incubation temperature is maintained at 37°±0.1° C. using a calibrated thermistor with a +/−0.1° C. accuracy. The look-up table for the temperature transducing thermistor 1000 is stored in a memory, and the temperature transducing thermistor 1000 is read every 3 seconds via a 12 bit A/D converter. This digital signal corresponds to the control signal for the feedback loop, and a microcontroller increases power applied to the heater when the apparent temperature drops below 36.9° C. and decreases applied power when the apparent temperature exceeds 37.1° C.

The exemplary vessel support 80 can also include an O-ring 41 that can be sandwiched in each well 45. An O-ring 41 so disposed along the interior of well 45 provides enough resistance to falling such that an analyte holding vessels 40 that is placed into a well 45 will not drop and splash the analyte. Moreover, such O-rings 41 are inexpensive and replaceable.

The exemplary vessel support 80 can also include an dual light pipe 675 that includes each of light pipes 60 and 70 inserted into the base of heat conducting block 85. Dual light pipe 675 can be used to maintain a constant spatial relationship between each of light pipes 60 and 70.

Finally, the exemplary vessel support 80 can also include a fixing dowel pin 6 that can be inserted into heat conducting block 85 used to fix the relative angular position of the heat conducting block 85 relative to any support or cover therefor.

Figure 10:
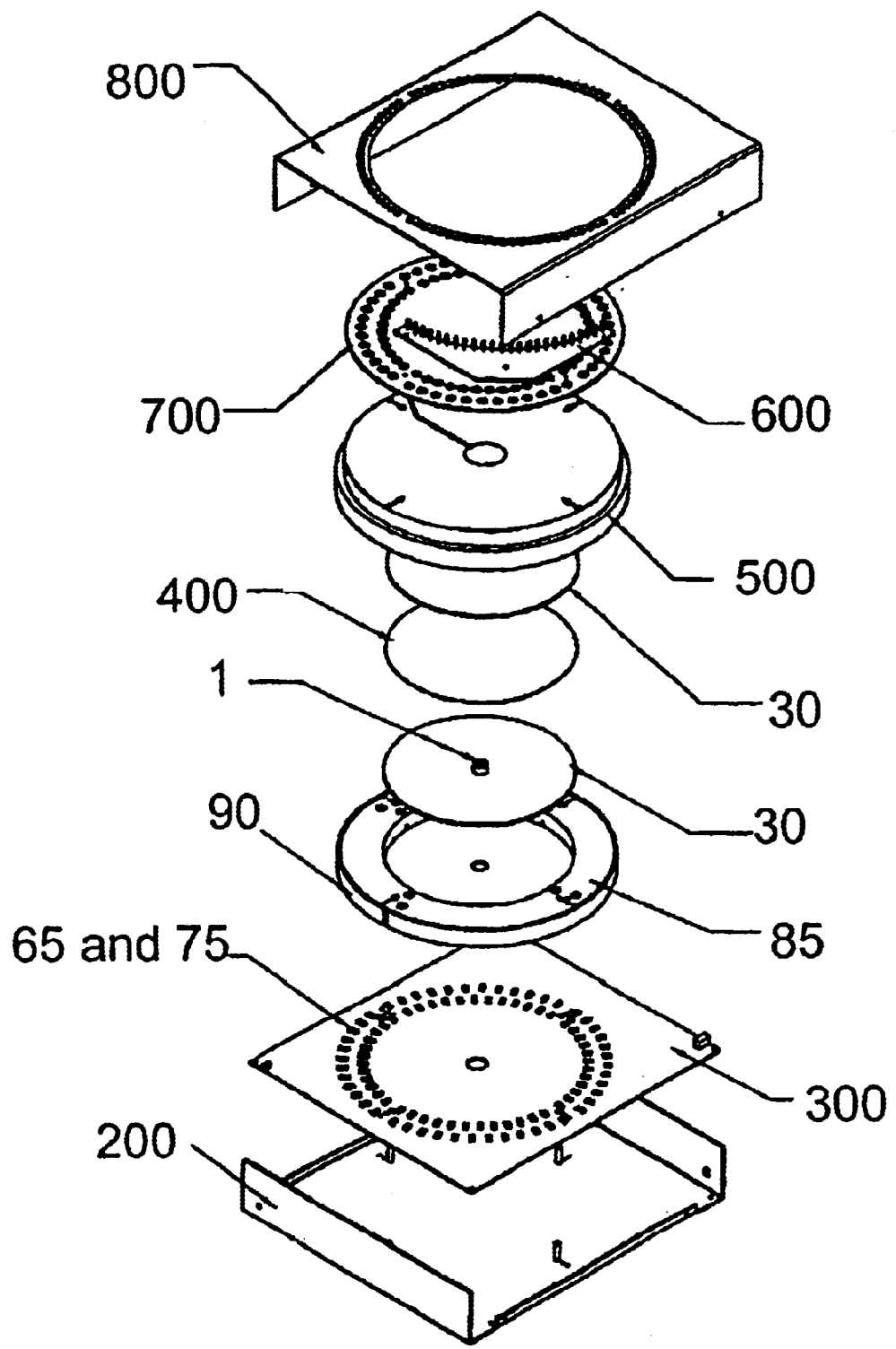
FIG. 10 illustrates an exploded view of an assay device according to the present invention.

FIG. 10 illustrates the assembly of an assay device according to the present invention. The device for assays is enclosed within a base 200 and a cover 800 that protect the optical and electronic components from, e.g., dust, water splashes, and other environmental hazards. In the illustrated embodiment, all light transducers 65 and 75 are arranged on a single printed circuit board assembly 300 to receive light output from a respective light pipe 60 or 70. Some or all electronic signal processing elements can be located on a single printed circuit board assembly 300, such as, e.g., timing elements, A/D converters, channel multiplexers, electrical filters, switches, and/or buffers. Either a raw or a processed (e.g., sampled and filtered) output from the individual light transducers 65 and 75 can be relayed to an external control/record processor by way of a multi-pin bulkhead connector (not shown) affixed to, e.g., the side wall of base 200. Naturally, plural printed circuit board assemblies 300 can be used in some embodiments of the invention.

Depending upon the thickness of heat conducting block 85, one or more LED source(s) 1 and radial waveguide(s) 30 can be disposed substantially concentrically within heater 90 and heat conducting block 85. If heat conducting block 85 is relatively thick, then one or more of the light paths 100 and 101 can pass through heat conducting block 85. This can be accomplished by boring radial holes to transmit the light emitted from radial waveguide(s) 30 through an analyte holding vessel 40 in a well 45 to a respective light pipe 60 or 70 which is affixed within heat conducting block 85. The respective light pipe 60 or 70, which can be fixed within a hole bored into the heat conducting block 85 in an axial direction, can then transmit the light to the respective light transducer 65 or 75 on printed circuit board assembly 300. As mentioned before, if further optical channels capable of making measurements upon a single analyte holding vessel 40 in a well 45 are added, then additional light pipes and light transducers can be added, as needed.

The illustrated device for assay has two separate radial waveguides 30 according to the first described embodiment, one which transmits light along light path 100 for assaying and one which transmits light along light path 101 for detecting an analyte holding vessel 40. Naturally, other numbers and types of radial waveguides 30 are available under the current invention. Moreover, one or more radial waveguide(s) 30 can be disposed such that they transmit light above heat conducting block 85 to a respective light pipe 60 or 70, which may or may not be affixed within the heat conducting block 85. In such a case, it may be desirable to optically isolate the individual analyte holding vessels 40 by interposing an opaque sheet between neighboring analyte holding vessels 40.

The two separate radial waveguides 30 are themselves optically isolated from one another through an optical separator 400. Such an optical separator can be formed, e.g., from a thin metallic or polymeric piece that is substantially opaque in the wavelengths used by the respective one or more LED source(s) 1.

In the illustrated embodiment, an insulating shell 500 is disposed and affixed atop the heat conducting block 85 and/or heater 90 to form vessel support 80. The insulating shell 500 can serves multiple purposes. Firstly, by thermally isolating the heat conducting block 85 and/or heater 90, the power requirements of the heater 90 can be reduced, and more uniform heating across the heat conducting block 85 can be obtained. Furthermore, even if insulating shell 500 were in physical contact with base 200, then conductive thermal transport to base 200 can be minimized. Moreover, since the insulating shell 500 reduces the power requirements of heater 90 for maintaining a substantially constant incubation temperature, a DC heater 90 can be used, which is easily amenable to microprocessor-based control and eliminates background electrical noise by removing a high power AC component from the assay device. This is particularly beneficial when a printed circuit board assembly 300 contains some and/or all of the processing equipment, since the base 200 and a cover 800 can form, in some embodiments, a Faraday cage with only DC power feed lines for the internal electronic circuitry.

Another advantage of the insulating shell 500 is that it allows for the minimization of the thickness of the conducting block 85 within the vessel support 80, and hence reduces the total weight of the instrument. For example, the insulating shell 500 can have a top face that is displaced from the conducting block 85 and holes (not shown) that support the analyte holding vessels 40 can be drilled through this top face. Thus, an analyte holding vessel 40 that is inserted into a well 45 is supported both at the conducting block 85 and at the insulating shell 500. The use of an insulating shell thus allows for the minimization of the thickness of conducting block 85 in the vessel support 80 while maintaining support for an analyte holding vessels 40 with a minimal increase in weight, since insulating shell 500 can be made from, e.g., a polymer. An example material for the insulating shell 500 is DELRIN (acetal).

Yet another advantage of the insulating shell 500 is that it can serve to fix the position of other components, including the O-rings 41 and the radial light guide(s) 20, relative to the conducting block 85 and wells 45.

In the embodiment illustrated in FIG. 10, an indicator assembly layer including a cover 700 and an LED indicator assembly 600 is included between the insulating shell 500 and the cover 800. Both the cover 700 and LED indicator assembly 600 can be used to provide a human operator with information regarding the wells 45. For example, an alphanumeric denominator for each well 45 can be included upon the cover 700 and the LED indicator assembly 600 can be used, e.g., to indicate to an operator that the assay device considers that an analyte holding vessel 40 has been inserted into a particular well 45. Thus, operator error due to incomplete and/or incorrect insertion of an analyte holding vessel 40 can be avoided.

Figure 11:
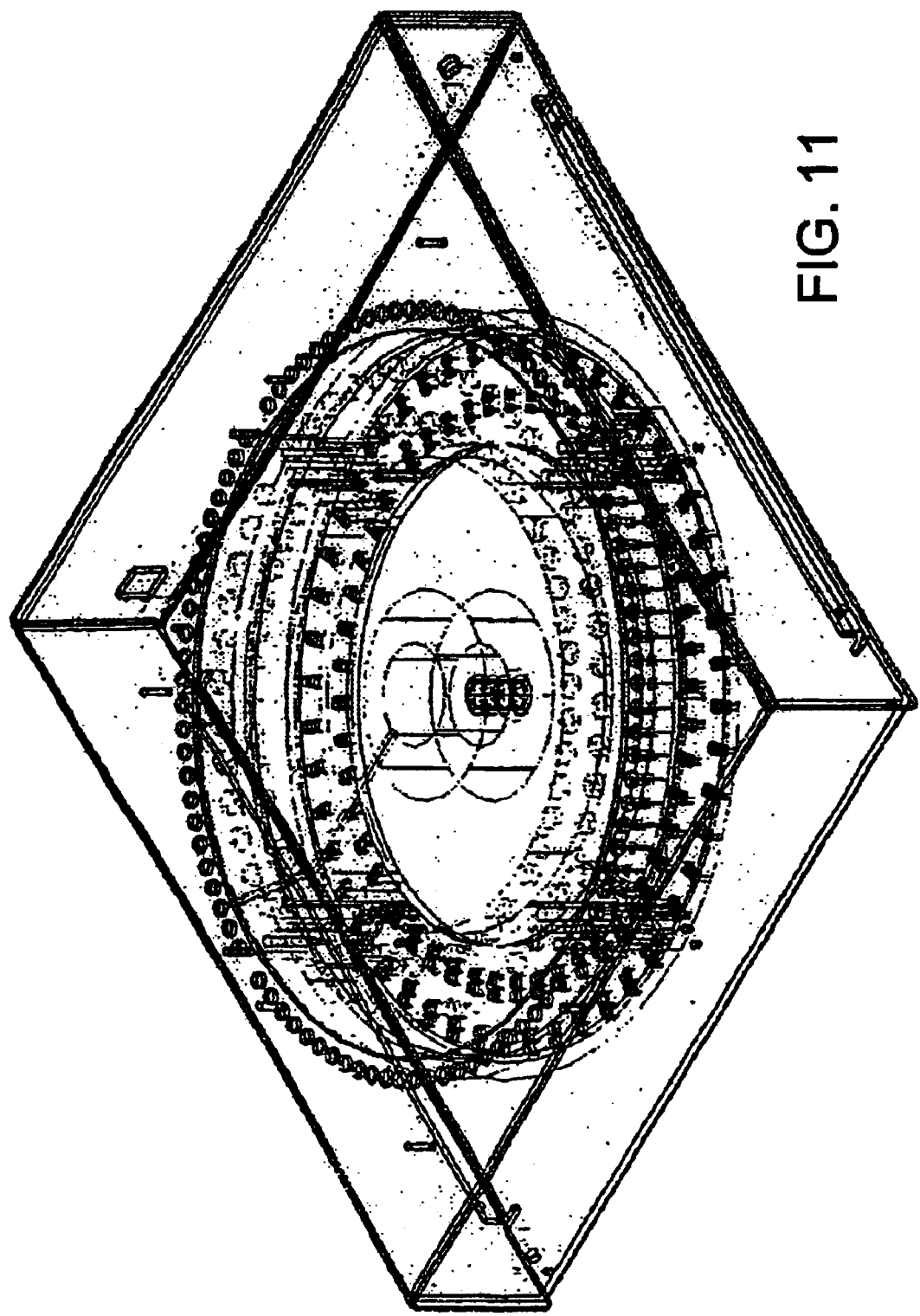
FIG. 11 illustrates a wireframe view of an exemplary assembled assay device.

FIG. 11 illustrates a wireframe view of an exemplary 96 well assembled assay device. The 96 wells in the illustrated exemplary device are arranged in two concentric circular rows about a center point which contains a real or virtual LED source 1. The locations of the wells 45 along the two rows are furthermore offset with regard to one another, so that a clear optical path to the outer wells from the real or virtual LED source 1 exists. Finally, there need not be any moving parts in the assay device, and moreover the entire device can be microprocessor controlled and DC powered.

Figure 12:
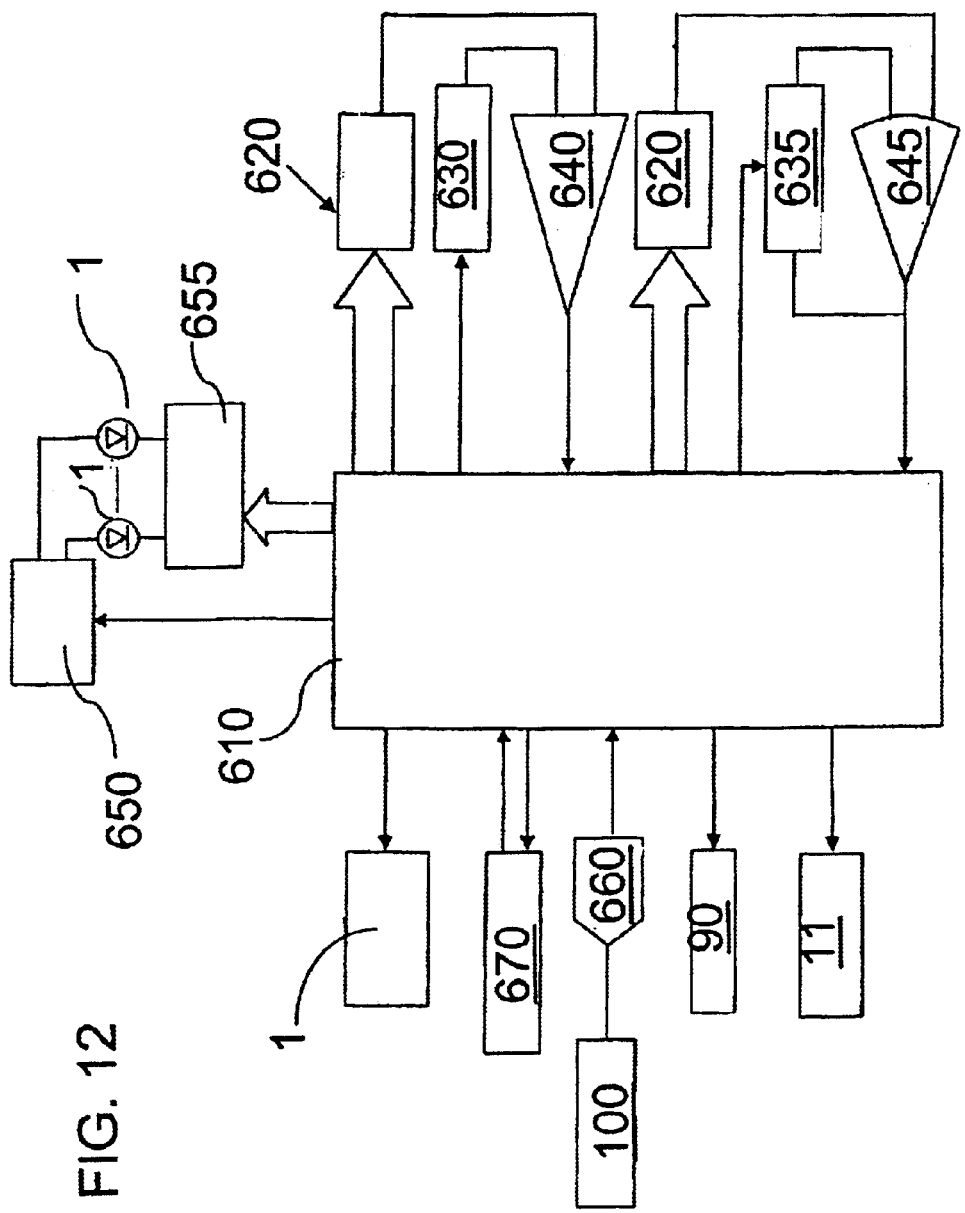
FIG. 12 illustrates an exemplary electronics block diagram of an assay device.

FIG. 12 illustrates an exemplary electronics block diagram of an assay device. As mentioned before, a single control/record processor 610 can be used to control operation of the elements of the assay device, as well as to record the results of the assays. For example, the resistance of thermistor 1000 can be measured by, e.g., placing thermistor 1000 in a bridge and digitizing a differential voltage across the bridge using an A/D convertor 660. The digitized differential voltage can be relayed to the control/record processor 610 which might have access to, e.g., a look-up table that associates certain differential voltages with certain temperatures. An exemplary commercially available control/record processor 610 is the Motorola P/N MC68HC711E9FN3. The control/record processor 610 can then compare the digitized differential voltage with a reference value, and increase and/or decrease the power output to heater 90 as needed. This will be discussed in more detail in regard to FIG. 14.

Another method of determining a temperature is through the use of a manufacturer-calibrated thermistor 1000. An R-T look-up table is provided by the manufacturer for such devices. In this case, the A/D converter 660 measures an absolute potential drop and hence resistance across the thermistor 1000.

Another function of the control/record processor 610 is implemented using a digital connection to an LED source 1 intensity controller 650. This intensity controller 650 can receive digital intensity control signals from the control/record processor 610 and use them to increase and/or decrease the bias voltage applied to one or more of the LED sources 1. This will be done, e.g., when an analyte holding vessel 40 is newly inserted into a particular well 45, or when an the light received by a light transducer 75 is too low in intensity for an accurate measurement to be made by a light transducer 75. The intensity controller 650 can also be used to modulate the bias voltage applied to the LED sources 1 as needed.

In order for the applied bias voltage to effect a light emission from the LED sources 1, a suitable voltage across the LED sources 1 must exist (i.e., the LED sources 1 must be forward biased). This too can be determined by the control/record processor 610, which uses a light source multiplexer 655 to selectively complete a return electrical current path through one or more particular LED sources 1. The light source multiplexer 655 can selectively forward bias an LED source 1 in response to, e.g., the insertion of an analyte holding vessel 40 into a particular well 45 serviced by an LED source 1, the selection of a certain assay wavelength by an operator corresponding to the emission of LED source 1, or simply to effect an on/off modulation as described in more detail in FIG. 15.

A separate vessel detect light source 1 is illustrated in FIG. 12 for the sake of illustrating separate control of the vessel detect optical path when a dedicated radial light guide 30 is used to form light path 101. This vessel detect light source 1 can also be formed by an LED and controlled using a light source multiplexer 655 and intensity controller 650 as described above.

Another way that the control/record processor 610 can respond to light transducer 75 receiving an insufficient light intensity is by changing an amplification gain for an amplifier associated with one or more light transducer(s) 75. This can be done by transmitting a well select signal to well selection unit 620 along with a digital gain adjust signal to the gain adjuster 635, which in turn can increase the gain of signal amplifier 645 for the selected well 45. The well selection unit 620 can be formed of another multiplexer that selects the output of a particular well 45 for input to the signal amplifier 645. Naturally, plural well selection units 620, signal amplifiers 645, and gain adjusters 635 can be used as well to produce a similar action.

A similar process can be used to adjust a light intensity cut-off level for determining when an analyte holding vessel 40 is present in one or more wells 45. Digital level adjuster 630 can be used to set an appropriate voltage for the vessel detect comparator 640 that is midway between the output voltage of light transducer 65 when an analyte holding vessel 40 is present and the output voltage of light transducer 65 when an analyte holding vessel 40 is absent from a well 45. A voltage set signal can be transmitted from control/record processor 610 to digital level adjuster 630 at the same time that the appropriate well is identified to well selection unit 620. Once again, plural well selection units 620, level adjusters 630, and vessel detect comparators 640 can be used as well to produce a similar action.

The control/record processor 610 can also be used to generate a ready signal, and error signal, and/or other indicator signals for output to indicator 11. The indicator 11 thus serves to provide operation information to an operator.

The control/record processor 610 can also be used to handle communications with another control/record processor 610, an output and/or input device, and/or with one or more computer-readable memory devices by way of a communications port 670. These functions will be discussed further in regard to FIG. 16.

Figure 13B:
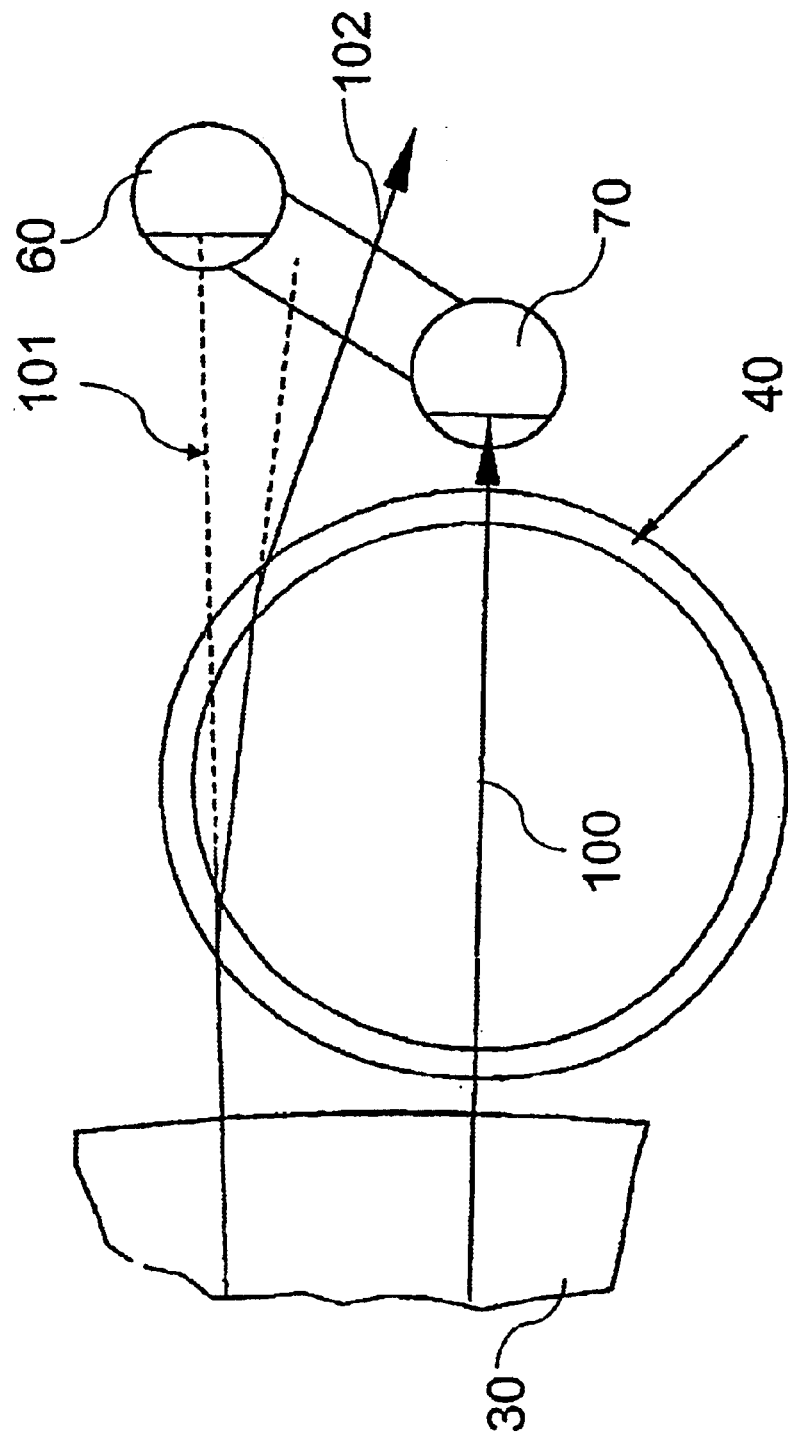
Figure 13C:
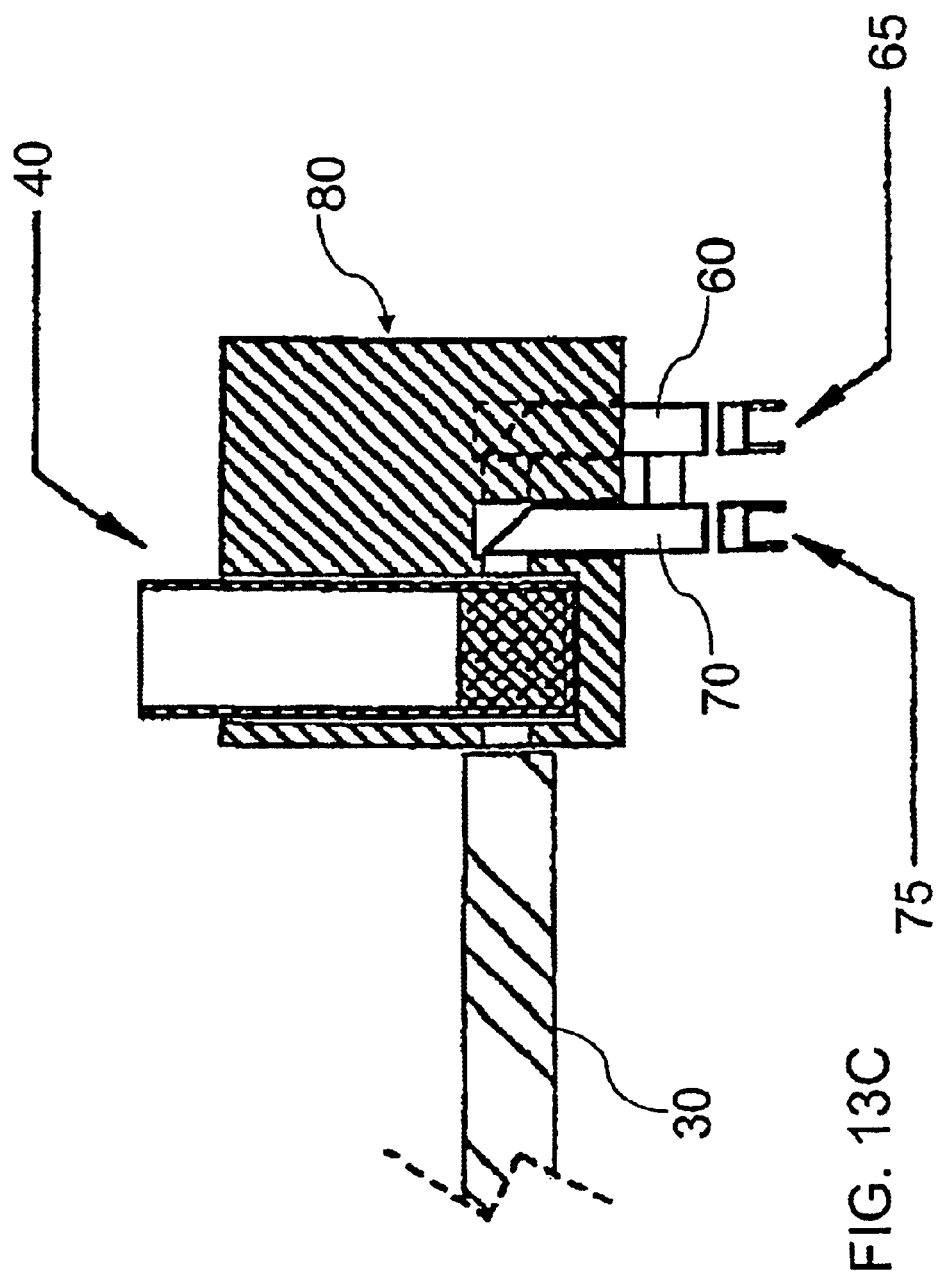

FIGS. 13A–C illustrate a top view in the absence of an analyte holding vessel 40, a top view in the presence of an analyte holding vessel 40, and a side view in the presence of an analyte holding vessel 40 that uses an exemplary side wall tube detection scheme with a single radial light guide 30. In the illustrated example, both the light paths 100 and 101 (as well as 102) pass through a single radial light guide 30 with the light path 101 simply being displaced by some angle from light path 100 within the single radial light guide 30. As illustrated, the side wall of the analyte holding vessel 40 deflects the path of light that travels down light path 101 without the analyte holding vessel 40 present in the well 45 to the light path 102 when the analyte holding vessel 40 is present in the well 45. This configuration is particularly advantageous when a flat-bottomed analyte holding vessel 40 as illustrated in FIG. 13C is used.

Furthermore, the side wall detection scheme illustrated in FIGS. 13A–C provides two further advantages. When the analyte holding vessel 40 is a test tube, the side wall curvature is often manufactured to tighter tolerances than the radius of the bottom of these vessels. As such, more reliable detection of these vessels can be obtained. Furthermore, regardless of the type of analyte holding vessel 40, sidewall detection allows the minimization of the length of light path 100. Since light pipe 70 can be brought closer to the well 45, the length of the light path 100 can be decreased, and the intensity of the light received by light pipe 70 increased.

Figure 14:
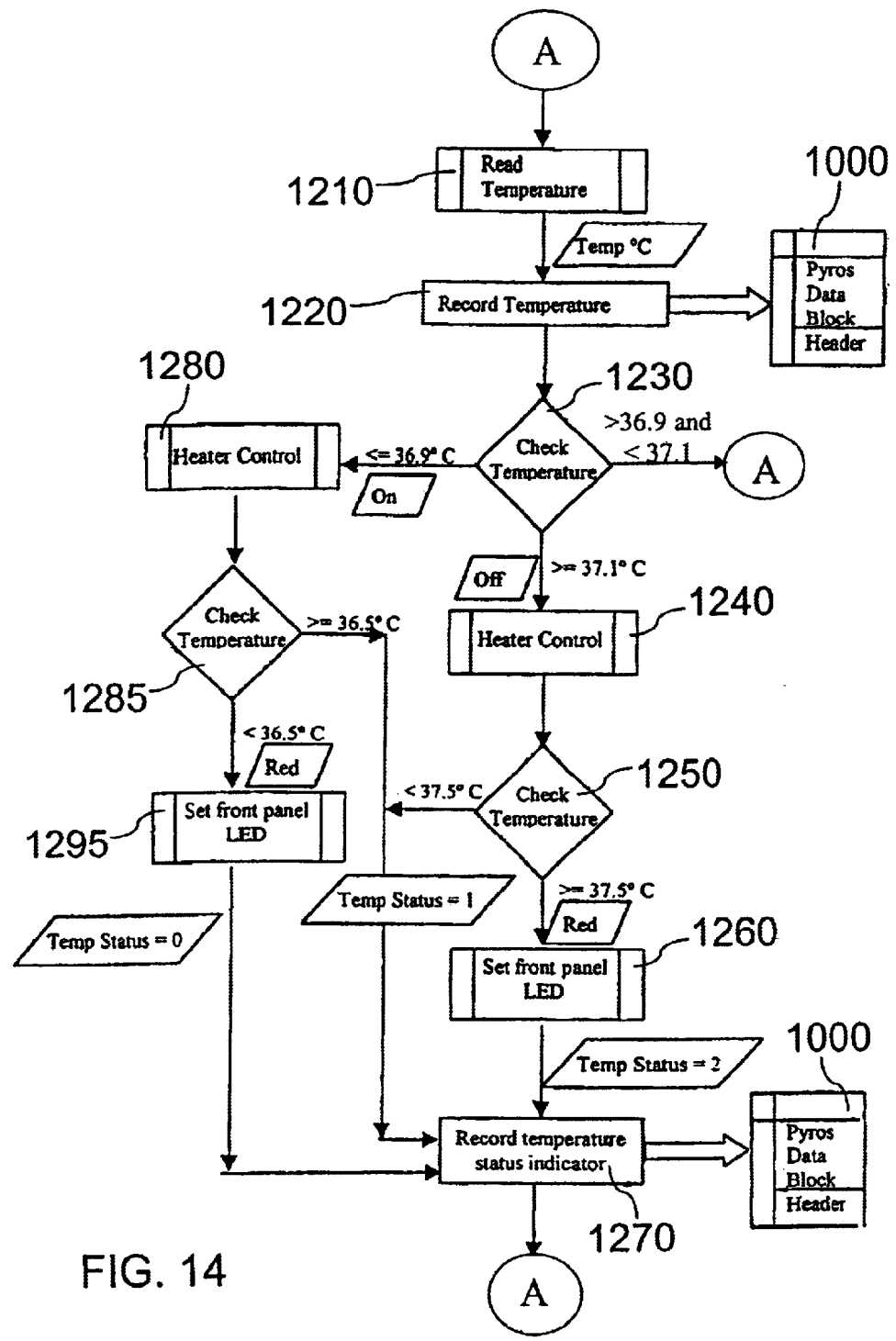
FIG. 14 illustrates an exemplary process loop for monitoring and controlling the incubation temperature according to the present invention.

FIG. 14 illustrates an exemplary process loop for monitoring and controlling the incubation temperature according to the present invention. In one embodiment, this process loop is performed at all times during operation of the assay device. In other words, an analyte holding vessel 40 need not be inserted into a well 45. In step 1210, the temperature is read using temperature transducing thermistor 1000 which can be precalibrated with corresponding temperature and resistances stored in a look-up table in computer-readable memory. Alternatively, temperature transducing thermistor 1000 can be linearized over a temperature range near a common incubation temperature such as 37.0° C. In either case, once a temperature (and/or corresponding resistance) has been determined, it is recorded in step 1220. This can be done by writing to a computer readable memory, such as the illustrated Pyros data block 1000. Recordation of the temperature in step 1220 need not always be performed. For example, in the case of a long assay time, only one in a certain number of measured temperatures need be recorded. Alternatively, if no analyte holding vessels 40 are located in a well 45, then temperature need not be recorded.

In step 1230, a determination is made as to whether the temperature read in step 1210 is within a certain range. In the illustrated process loop, if the read temperature is less than 37.1° C. and greater than 36.9° C., then the process flow returns to step 1210, perhaps after a suitable delay. However, if the read temperature is less than 36.9° C., then the process flow proceeds to step 1280, where the heater control indicates that the power to the heater 90 should be increased. In step 1285, another determination is made as to whether the temperature read in step 1210 falls within a certain range.

The determination in step 1285 is made to determine whether a critical temperature situation due to underheating exists. For example, if the read temperature is less than 36.5° C., then a critical situation is indicated to the operator by setting a front panel LED indicator to red in step 1295. The assay device also sets an internal status indicator to a value, e.g., 0, that indicates the presence of a critical temperature situation due to underheating. After the critical temperature situation is indicated to both the user and/or other portions of the device, both the temperature and status is recorded in step 1270 by writing to, e.g., the illustrated Pyros data block 1000. After recordation of the temperature and status, the process flow loops back to step 1210.

In step 1235, if it is determined that a critical temperature situation does not exist, then the process flow proceeds to step 1270 without indicating a critical temperature situation to the user and/or other portions of the device. Once again, both the temperature and status can be recorded in step 1270 as needed by writing to, e.g., the illustrated Pyros data block 1000. After recordation of the temperature and status, the process flow loops back to step 1210.

In step 1230, if the read temperature is greater than 37.1° C., then the process flow proceeds to step 1240, where the heater control indicates that the power to the heater 90 should be decreased and/or cut off. In step 1250, another determination is made as to whether the temperature read in step 1210 falls within a certain range. The determination in step 1250 is made to determine whether a critical temperature situation due to overheating exists. For example, if the read temperature is greater than 37.5° C., then a critical situation is indicated to the operator by setting a front panel LED indicator to red in step 1260. The assay device also sets an internal status indicator to a value, e.g., 2, that indicates the presence of a critical temperature situation due to overheating. After the critical temperature situation is indicated to both the user and/or other portions of the device, both the temperature and status can be recorded in step 1270 by writing to, e.g., the illustrated Pyros data block 1000. After recordation of the temperature and status, the process flow loops back to step 1210.

In step 1250, if it is determined that a critical temperature situation does not exist, then the process flow proceeds to step 1270 without indicating a critical temperature situation to the user and/or other portions of the device. Once again, both the temperature and status can be recorded in step 1270 by writing to, e.g., the illustrated Pyros data block 1000. After recordation of the temperature and status, the process flow loops back to step 1210.

Figure 15:
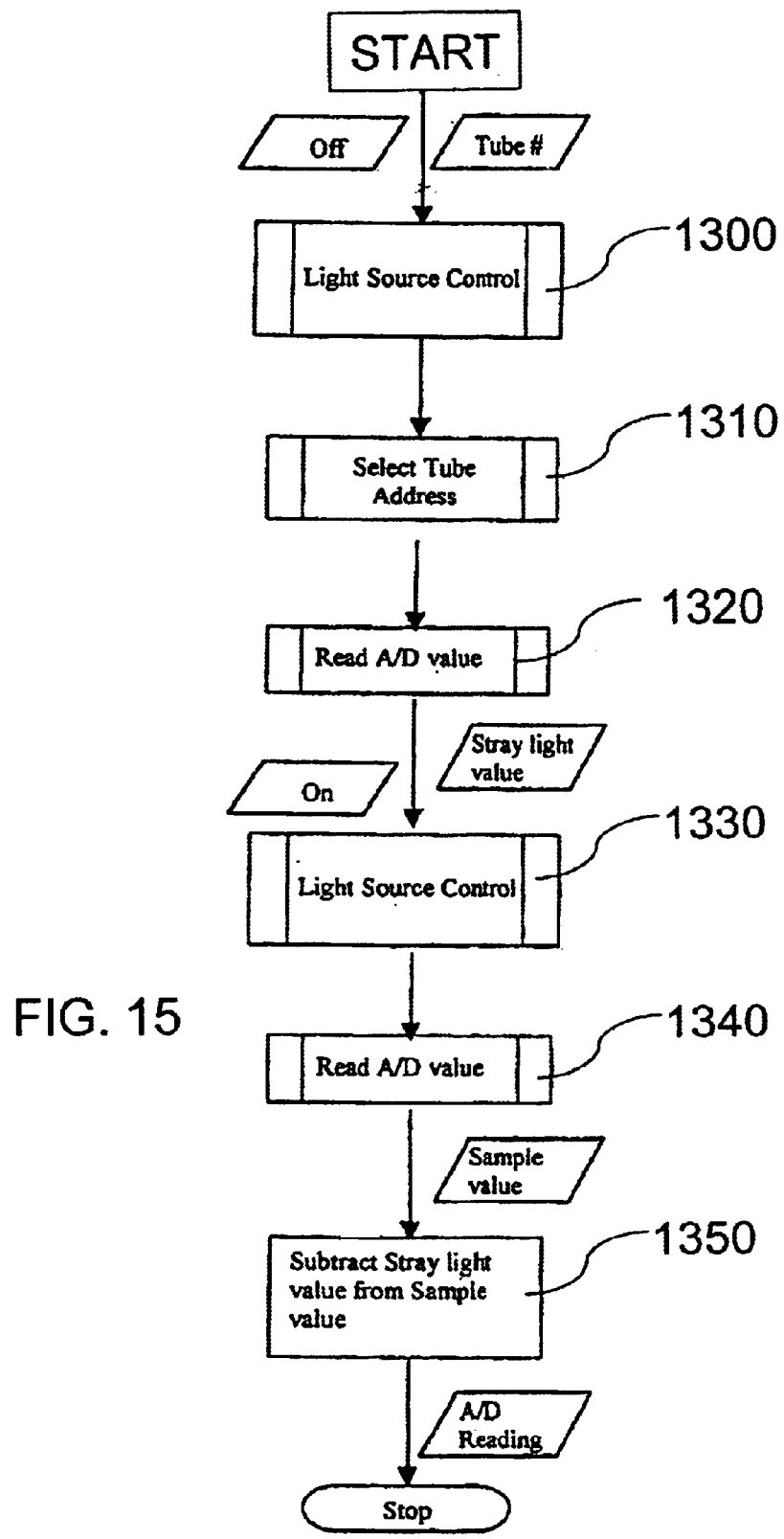
FIG. 15 illustrates a process flow for an exemplary on/off modulation of the light output by LED source 1 for background correction.

FIG. 15 illustrates a process flow for an exemplary on/off modulation of the light output by LED source 1 for background correction. In the on/off modulation, a background light level is first determined for a particular light transducer, and then a transmitted light measurement is performed. The background level can thus be subtracted out, and more accurate measurements made. In step 1300, a LED source 1 that provides the majority of the illumination for a particular well 45 is shut off. In a preferred embodiment, a particular well 45 already has an analyte holding vessel 40 inserted therein. The particular well 45 can be operator-identified, or the instrument can constantly cycle around all available (e.g., filled) wells 45 and the particular well 45 can just happen to be a next well in line. In either case, the address of the particular well 45 is selected in step 1310 so that a background output of the light transducer 75 (and even a light transducer 65, as needed) can be digitized and/or otherwise processed for storage. Thereafter, in step 1320, the background output of the light transducer 75 is read and/or digitized. After information related to the background output of the light transducer 75 has been stored, the process flow proceeds to step 1330 where the LED source 1 that provides the majority of the illumination for a particular well 45 is turned on. The light transmitted through the analyte holding vessel 40 when the LED source 1 is turned on is termed the "sample value." In step 1340, one or more "sample values" are read over a period of time so that the contents of the analyte holding vessel 40 can be, e.g., turbidometrically and chromogenically assayed. Before the read "sample values" are, e.g., displayed and/or stored in a computer-readable memory, the read background output of the light transducer 75 is subtracted from the "sample values." Naturally, both the unchanged "sample values" and the read background output of the light transducer 75 can be stored and the subtraction operation performed, e.g., only upon the request of an operator.

Modulation of the intensity of emitted light from LED source 1 need not be implemented as described (single step on/off) in regard to FIG. 15. For example, a sinusoidal modulation of the output intensity of LED source 1 with phase locking can be used to discriminate between the light originating from a particular LED source 1 and background (including other LED sources 1, provided the other sources aren't similarly modulated). As another example, the on/off modulation can occur continuously during assaying, so that a continuous measurement of background is made.

As another example of a useful modulation, the light emitted from LED source 1 can be controlled to follow a predetermined intensity as a function of time. This intensity as a function of time can be selected, e.g., to mimic the intensity as a function of time that would be observed if a particular assay were being performed. Thus, if all analyte holding vessels 40 are removed from the wells 45, then the light from a single LED source 1 can be substantially uniformly transmitted to plural (or even all) light transducers 75 simultaneously. Thus, the measured intensities for each of the separate optical channels can be compared and each optical channel can be calibrated.

Figure 16:
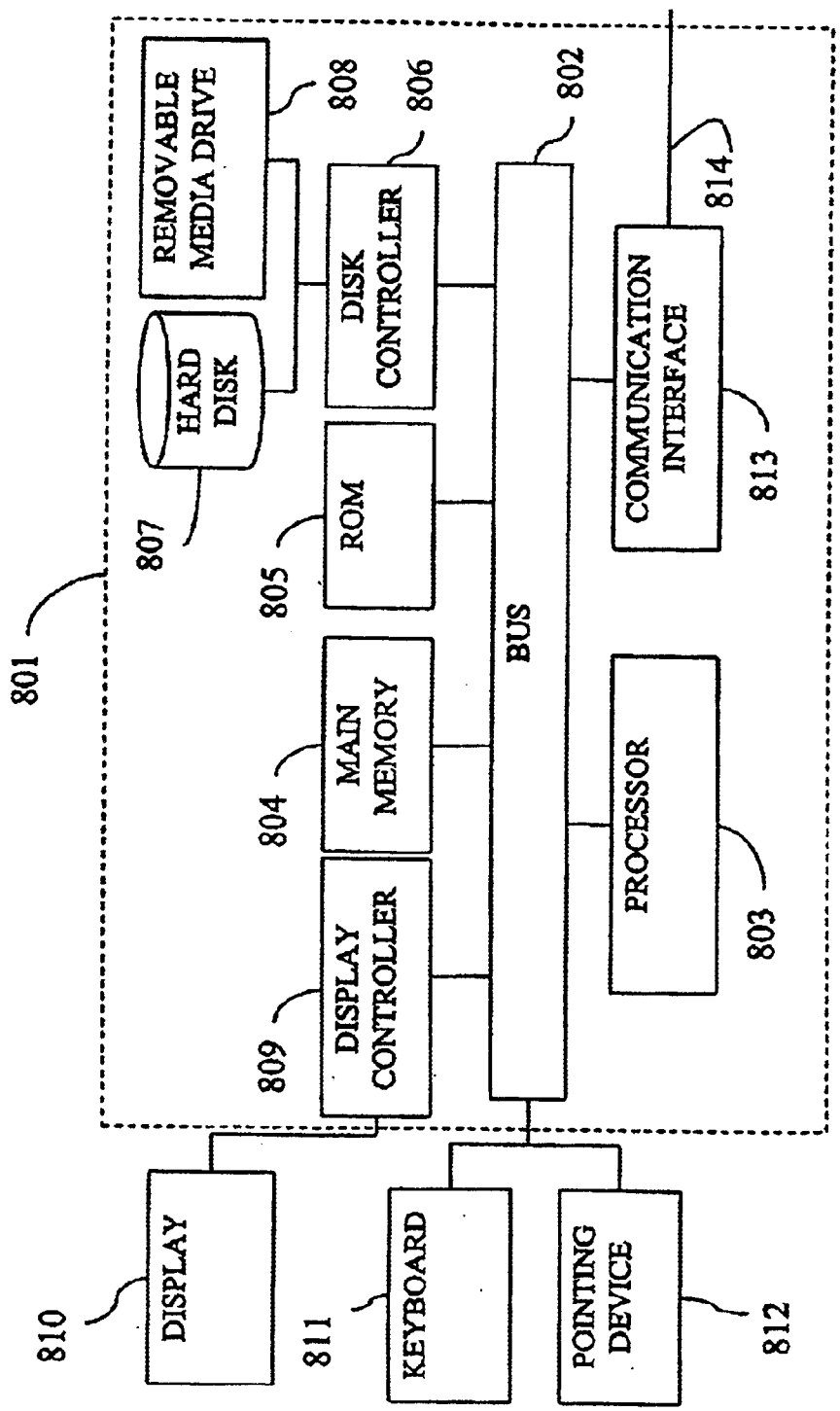
FIG. 16 illustrates an exemplary computer system 801 that can form an external control/record processor in an embodiment of the present invention.

FIG. 16 illustrates a computer system 801 that can form an external control/record processor in an embodiment of the present invention. For example, computer system 801 can communicate with control/record processor 610 of FIG. 12 by way of communications port 670.

Computer system 801 includes a bus 802 or other communication mechanism for communicating information, and a processor 803 coupled with bus 802 for processing the information. Computer system 801 also includes a main memory 804, such as a random access memory (RAM) or other dynamic storage device (e.g., dynamic RAM (DRAM), static RAM (SRAM), synchronous DRAM (SDRAM), flash RAM), coupled to bus 802 for storing information and instructions to be executed by processor 803. In addition, main memory 804 may be used for storing temporary variables or other intermediate information during execution of instructions to be executed by processor 803. Computer system 801 further includes a read only memory (ROM) 805 or other static storage device (e.g., programmable ROM (PROM), erasable PROM (EPROM), and electrically erasable PROM (EEPROM)) coupled to bus 802 for storing static information and instructions for processor 803. A storage device 807 and/or 808, such as a magnetic disk or optical disk, is provided and coupled to bus 802 by way of a disk controller 806 for storing information and instructions. Storage device 807 and/or 808 can contain the tables that record operating and/or measurement information, such as the Pyros data block 1000 of FIG. 14.

The computer system 801 may also include special purpose logic devices (e.g., application specific integrated circuits (ASICs)) or configurable logic devices (e.g., generic array of logic (GAL) or reprogrammable field programmable gate arrays (FPGAs)). Other removable media devices (e.g., a compact disc, flash memory cards, a tape, and a removable magneto-optical media) or further fixed, high density media drives, may be added to the computer system 801 using an appropriate device bus (e.g., a small computer system interface (SCSI) bus, an enhanced integrated device electronics (IDE) bus, or an ultra-direct memory access (DMA) bus). Such removable media devices and fixed, high density media drives can also contain the tables that record operating and/or measurement information, such as the Pyros data block 1000 of FIG. 14. The computer system 801 may additionally include a compact disc reader, a compact disc reader-writer unit, or a compact disc juke box, each of which may be connected to the same device bus or another device bus.

Computer system 801 may be coupled via bus 802 to a display 810, such as a cathode ray tube (CRT), for displaying information to a computer user. Display 810 can perform the functions of an indicator 11 as seen in FIG. 12, especially when the assay device is operated remotely from the computer system 801. The display 810 may be controlled by a display or graphics card. The computer system includes input devices, such as a keyboard 811 and a pointing device 812 (e.g., a cursor control), for communicating information and command selections to processor 803. The pointing device 812 (e.g., cursor control), for example, is a mouse, a trackball, or cursor direction keys for communicating direction information and command selections to processor 803 and for controlling cursor movement on the display 810.

The computer system 801 can perform a portion or all of the processing steps of the invention in response to processor 803 executing one or more sequences of one or more instructions contained in a memory, such as the main hard disk memory 807. Such instructions may be read into the main hard disk memory 807 from another computer readable medium, such as storage device 808. One or more processors in a multi-processing arrangement may also be employed to execute the sequences of instructions contained in main hard disk memory 807. In alternative embodiments, hard-wired circuitry may be used in place of or in combination with software instructions. Thus, embodiments are not limited to any specific combination of hardware circuitry and software.

As stated above, the system 801 includes at least one computer readable medium or memory programmed according to the teachings of the invention and for storing data structures, tables, records, or other data described herein. Examples of computer readable media are compact discs, hard disks, floppy disks, tape, magneto-optical disks, PROMs (EPROM, EEPROM, Flash EPROM), DRAM, SRAM, SDRAM, etc. Stored on any one or on a combination of computer readable media, the present invention includes software for controlling the computer system 801, for driving a device or devices for implementing the invention, and for enabling the computer system 801 to interact with a human user. Such software may include, but is not limited to, device drivers, operating systems, development tools, and applications software. Such computer readable media further includes the computer program product of the present invention for performing all or a portion (if processing is distributed) of the processing performed in implementing the invention.

The computer code devices of the present invention may be any interpreted or executable code mechanism, including but not limited to scripts, interpreters, dynamic link libraries, Java classes, and complete executable programs. Moreover, parts of the processing of the present invention may be distributed for better performance, reliability, and/or cost.

The term "computer readable medium" as used herein refers to any medium or media that participate in recording data and/or providing instructions to processor 803 for execution. A computer readable medium may take many forms, including but not limited to, non-volatile media, volatile media, and transmission media. Non-volatile media includes, for example, optical, magnetic disks, and magneto-optical disks, such as storage device 807 and/or 808. Transmission media includes coaxial cables, copper wire and fiber optics, including the wires that comprise bus 802. Transmission media also may also take the form of acoustic or light waves, such as those generated during radio wave and infrared data communications.

Common forms of computer readable media include, for example, hard disks, floppy disks, tape, magneto-optical disks, PROMs (EPROM, EEPROM, Flash EPROM), DRAM, SRAM, SDRAM, or any other magnetic medium, compact disks (e.g., CD-ROM), or any other optical medium, punch cards, paper tape, or other physical medium with patterns of holes, a carrier wave (described below), or any other medium from which a computer can read.

Various forms of computer readable media may be involved in carrying out one or more sequences of one or more instructions to processor 803 for execution. For example, the instructions may initially be carried on a magnetic disk of a remote computer. The remote computer can load the instructions for implementing all or a portion of the present invention remotely into a dynamic memory and send the instructions over a telephone line using a modem. A modem local to computer system 801 may receive the data on the telephone line and use an infrared transmitter to convert the data to an infrared signal. An infrared detector coupled to bus 802 can receive the data carried in the infrared signal and place the data on bus 802. Bus 802 carries the data to main hard disk memory 807, from which processor 803 retrieves and executes the instructions. The instructions received by main hard disk memory 807 may optionally be stored on a removable media storage device 808 either before or after execution by processor 803.

Computer system 801 also includes a communication interface 813 coupled to bus 802. Communication interface 813 can be connected to communication port 670 of an internal control/record processor 610, or internal control/record processor 610 can be eliminated in whole or in part and the communication interface 813 can conduct direct communications with, e.g., level adjuster 630 and gain adjuster 635. In any such implementation, communication interface 813 sends and receives electrical, electromagnetic, or optical signals that carry data representing various types of information.

Obviously, numerous modifications and variations of the present invention are possible in light of the above teachings. It is therefore to be understood that within the scope of the appended claims, the invention may be practiced otherwise than as specifically described herein.

What is claimed is:

1. An assay device, comprising:
   a LED source configured to generate a light;
   a radial waveguide configured to receive a portion of said light generated by said LED source and radially distribute said portion of said light;
   a plurality of vessel wells each configured to receive an analyte vessel and disposed radially to said radial waveguide; and a plurality of light transducers each configured to transduce a transmitted portion of said light radially distributed by said radial waveguide that has passed through said vessel well.

2. The assay device according to claim 1, further comprising:
a second LED source configured to generate a second light;
a second radial waveguide configured to receive a portion of said second light generated by said second LED source and radially distribute said portion of said second light to said plurality of vessel wells; and
a second plurality of light transducers each configured to transduce a portion of said second light radially distributed by said second radial waveguide that has passed through said vessel well.

3. The assay device according to claim 2, wherein said second radial waveguide comprises a plurality of wedge waveguides.

4. The assay device according to claim 1, wherein said radial waveguide comprises a plurality of wedge waveguides.

5. The assay device according to claim 4, wherein each of said plurality of wedge waveguides comprises a curved wedge waveguide.

6. The assay device according to claim 4, wherein each of said plurality of wedge waveguides comprises a lensmatic wedge waveguide.

7. The assay device according to claim 1, further comprising a second plurality of light transducers each configured to transduce a portion of said light radially distributed by said radial waveguide that has passed through said vessel well.

8. The assay device according to claim 7, wherein said second plurality of light transducers transduces light that has passed through a side portion of said vessel well.

9. The assay device according to claim 7, wherein said second plurality of light transducers transduces light that has passed through a bottom portion of said vessel well.

10. The assay device according to claim 7, wherein said second plurality of light transducers is used to detect a presence of said analyte vessel in said vessel well.

11. The assay device according to claim 1, further comprising a modulator configured to modulate an intensity of said light generated by said LED source.

12. The assay device according to claim 11, wherein said modulator is configured to turn on and off said LED source.

13. The assay device according to claim 1, wherein said LED source generates light having a wavelength of 470 nm +/−30 nm.

14. The assay device according to claim 1, further comprising an optical filter.

15. The assay device according to claim 14, wherein said optical filter is disposed along an optical path between said LED source and said radial waveguide.

16. The assay device according to claim 1, wherein said plurality of vessel wells is disposed in a substantially circular geometry around said LED source.

17. The assay device according to claim 1, wherein said plurality of vessel wells comprises two concentric circular rows of said vessel wells around said LED source, wherein vessel wells of said two concentric circular rows are staggered to receive said light radially distributed by said radial waveguide.

18. The assay device according to claim 1, further comprising a plurality of light pipes configured to reflect and conduct said transmitted portion of said light that has passed through said vessel well to said plurality of light transducers.

19. The assay device according to claim 18, wherein said plurality of light pipes is configured to reflect and conduct said transmitted portion of said light that has passed through said vessel well downward.

20. The assay device according to claim 19, wherein said plurality of light transducers are disposed in a single plane.

21. The assay device according to claim 18, further comprising a printed circuit board supporting said plurality of light transducers.

22. The assay device according to claim 1, further comprising a plurality of printed circuit boards supporting said plurality of light transducers.

23. The assay device according to claim 1, further comprising a vessel support configured to contain said plurality of vessel wells.

24. The assay device according to claim 23, wherein said vessel support comprises:
a heat conducting portion configured to transmit heat to said analyte vessel in said vessel wells; and
a heater configured to maintain said heat conducting portion substantially at an incubation temperature.

25. The assay device according to claim 23, wherein said vessel support further comprises:
a heat insulating portion configured to thermally insulate said heat conducting portion.

26. The assay device according to claim 24, wherein said heater comprises a DC heater.

27. The assay device according to claim 24, wherein:
said heater comprises a ring heater; and
said heat conducting portion comprises a heat conducting ring.

28. The assay device according to claim 27, wherein said ring heater is disposed around said heat conducting ring.

29. The assay device according to claim 1, further comprising a precalibrated temperature transducer.

30. The assay device according to claim 24, further comprising a precalibrated temperature transducer disposed within said heat conducting portion.

31. An assay device, comprising:
a light source configured to generate a light;
a plurality of vessel wells each configured to receive an analyte vessel and disposed in an optical path of a portion of said light generated by said light source;
a plurality of optical pipes each configured to receive said portion of said light transmitted along a respective of said optical paths through a respective of said plurality of vessel wells and reflect and conduct said received light; and
a single printed circuit board including a plurality of light transducers each configured to transduce a portion of said light reflected and conducted by a respective of said plurality of optical pipes.

32. An assay device, comprising:
a light source configured to generate a light;
a plurality of vessel wells each configured to receive an analyte vessel and disposed in an optical path of a portion of said light generated by said light source;
a plurality of optical pipes each configured to receive said portion of said light transmitted along a respective of said optical paths through a respective of said plurality of vessel wells and reflect and conduct said received light downward, a first of said plurality of optical pipes configured to receive light through a first portion of a vessel disposed in one of said plurality of vessel wells and a second of said plurality of optical pipes configured to receive light through a second portion of the vessel disposed in the one of said plurality of vessel wells; and a printed circuit board disposed below said plurality of vessel wells and including a light transducer configured to transduce a portion of said light reflected and conducted by a respective of said plurality of optical pipes.

33. A method for performing assays comprising:

generating light using a LED;

radially guiding a portion of the generated light;

transmitting a portion of the guided light through a plurality of vessels; and transducing a portion of the transmitted light to perform an assay.

34. The method according to claim 33, wherein said transmitting step further comprises transmitting a second portion of said guided light through one of a side and a bottom portion of said plurality of vessels to detect the presence of said plurality of vessels.

35. The method according to claim 33, further comprising reflecting said transmitted light from a plurality of vessels in a same direction.

36. The method according to claim 33, further comprising diverging said portion of said generated light.

37. The method according to claim 36, wherein said diverging step and said radially guiding step are performed by a same light guide.

38. The method according to claim 33, further comprising modulating an intensity of said portion of the transmitted light.

39. The method according to claim 38, wherein said modulating step comprises modulating a generated light intensity.

40. The method according to claim 38, wherein said modulating step comprises alternatively starting and stopping said generating of light.

41. The method according to claim 38, further comprising correcting for a background light intensity.

42. A device for performing assays, comprising:

means for generating light;

means for radially guiding a portion of the generated light;

means for transmitting a portion of the guided light through a plurality of vessels; and means for transducing a portion of the transmitted light to perform an assay.

43. An assay device, comprising:

a LED source configured to generate a light;

radial waveguide means for receiving a portion of said light generated by said LED source and radially distribute said portion of said light;

a plurality of vessel wells each configured to receive an analyte vessel and disposed radially to said radial waveguide means; and a plurality of light transducer means for transducing a transmitted portion of said light radially distributed by said radial waveguide means that has passed through said vessel well.

44. The assay device according to claim 43, further comprising:

a second LED source configured to generate a second light;

second radial waveguide means for receiving a portion of said second light generated by said second LED source and radially distribute said portion of said second light to said plurality of vessel wells; and a second plurality of light transducer means for transducing a portion of said second light radially distributed by said second radial waveguide means that has passed through said vessel well.

45. The assay device according to claim 44, wherein said second radial waveguide means comprises a plurality of wedge waveguide means.

46. The assay device according to claim 44, wherein said radial waveguide means comprises a plurality of wedge waveguide means.

47. The assay device according to claim 46, wherein each of said plurality of wedge waveguide means comprise a curved wedge waveguide.

48. The assay device according to claim 46, wherein each of said plurality of wedge waveguide means comprises a lensmatic wedge waveguide means.

49. The assay device according to claim 43, further comprising a second plurality of light transducer means for transducing a portion of said light radially distributed by said radial waveguide means that has passed through said vessel well.

50. The assay device according to claim 49, wherein said second plurality of light transducer means transduces light that has passed through a side portion of said vessel well.

51. The assay device according to claim 49, wherein said second plurality of light transducer means transduces light that has passed through a bottom portion of said vessel well.

52. The assay device according to claim 49, wherein said second plurality of light transducer means comprises transducer means for detecting a presence of said analyte vessel in said vessel well.

53. The assay device according to claim 43, further comprising a means for modulating an intensity of said light generated by said LED source.

54. The assay device according to claim 53, wherein said means for modulating comprised a means for turning on and off said LED source.

55. The assay device according to claim 43, wherein said LED source generates light having a wavelength of 470 nm +/−30 nm.

56. The assay device according to claim 43, further comprising a means for filtering a light.

57. The assay device according to claim 56, wherein said means for filtering is disposed along an optical path between said LED source and said radial waveguide means.

58. The assay device according to claim 43, wherein said plurality of vessel wells are disposed in a substantially circular geometry around said LED source.

59. The assay device according to claim 43, wherein said plurality of vessel wells comprises two concentric circular rows of said vessel wells around said LED source, wherein vessel wells of said two concentric circular rows are staggered to receive said light radially distributed by said radial waveguide.

60. The assay device according to claim 43, further comprising a plurality of means for reflecting and conducting said transmitted portion of said light that has passed through said vessel well to said plurality of light transducer means.

61. The assay device according to claim 60, wherein said means for reflecting and conducting are configured to reflect said transmitted portion of said light that has passed through said vessel well downward.

62. A The assay device according to claim 61, wherein said plurality of light transducer means are disposed in a single plane.

63. The assay device according to claim 60, further comprising a means for supporting said plurality of light transducers.

64. The assay device according to claim 43, further comprising a plurality of means for supporting said plurality of light transducers.

65. The assay device according to claim 43, further comprising a means for supporting said plurality of vessel wells.

66. The assay device according to claim 65, wherein said means for supporting comprises:
  means for conducting heat to said analyte vessel in said vessel wells; and
  means for maintaining said means for conducting substantially at an incubation temperature.

67. The assay device according to claim 65, wherein said vessel support further comprises:
  means for thermally insulating said means for conducting.

68. The assay device according to claim 66, wherein said means for maintaining comprises a DC means for maintaining.

69. The assay device according to claim 66, wherein:
  said means for maintaining comprises an annular means for maintaining; and
  said means for conducting comprises an annular means for conducting.

70. The assay device according to claim 69, wherein said annular means for maintaining is disposed around said annular means for conducting.

71. The assay device according to claims 43, further comprising a precalibrated means for transducing temperature.

72. The assay device according to claim 66, further comprising a precalibrated means for transducing temperature disposed within said means for conducting.

73. An assay device, comprising:
  means for generating a light;
  plural means for receiving an analyte vessel, each disposed along an optical path of a portion of said light generated by said light generating means;
  a plurality of means for redirecting light, each configured to receive said portion of said light transmitted along a respective of said optical paths through a respective one of said plurality of means for receiving, a first of said plurality of means for redirecting light configured to receive light through a first portion of a vessel disposed in one of said plural means for receiving an analyte vessel and a second of said plurality of means for redirecting light configured to receive light through a second portion of the vessel disposed in the one of said plural means for receiving an analyte vessel; and
  a single means for supporting a plurality of means for transducing a portion of said light reflected by said plurality of means for redirecting light.

74. An assay device, comprising:
  means for generating a light;
  plural means for receiving an analyte vessel, each disposed along an optical path of a portion of said light generated by said light generating means;
  a plurality of means for redirecting light downward, each configured to receive said portion of said light transmitted along a respective of said optical paths through a respective of said plurality of means for receiving, a first of said plural means for redirecting light configured to receive light through a first portion of a vessel disposed in one of said plural means for receiving an analyte vessel and a second of said plural means for redirecting light configured to receive light through a second portion of the vessel disposed in the one of said plural means for receiving an analyte vessel; and
  a means for transducing a portion of said light reflected downward by said plurality of means for redirecting light.

75. The assay device according to claim 1, wherein said LED source generates light having a wavelength of 430 nm +/−30 nm.

76. The assay device according to claim 1, wherein said LED source generates light having a wavelength less than 720 nm.

77. The assay device according to claim 11, wherein said modulator comprises a control processor.

78. The assay device according to claim 31, further comprising a radial waveguide optically coupled intermediate the light source and at least one of the plurality of vessel wells.

79. The assay device according to claim 32, further comprising a radial waveguide optically coupled intermediate the light source and at least one of the plurality of vessel wells.

80. The assay device according to claim 73, further comprising a radial waveguide optically coupled intermediate the means for generating light and at least one of the plural means for receiving an analyte of vessel.

81. The assay device according to claim 74, further comprising a radial waveguide optically coupled intermediate the means for generating light and at least one of the plural means for receiving an analyte of vessel.

82. The assay device according to claim 31, wherein a first of said plurality of optical pipes is configured to receive light through a first portion of a vessel disposed in one of said plurality of vessel wells and a second of said plurality of optical pipes is configured to receive light through a second portion of the vessel disposed in the one of said plurality of vessel wells.

83. An assay device, comprising:
  a light source configured to generate a light;
  a plurality of vessel wells each configured to receive an analyte vessel and disposed in an optical path of a portion of said light generated by said light source;
  a plurality optical pipes each configured to receive said portion of said light transmitted along a respective of said optical paths through a respective of said plurality of vessel wells and reflect and conduct said received light downward; and
  a printed circuit board disposed below said plurality of vessel wells and including a plurality of light transducers configured to transduce a portion of said light reflected and conducted by a respective of said plurality of optical pipes.

84. The assay device of claim 82, wherein the plurality of optical pipes comprises a first optical pipe configured to receive light through a first portion of a vessel disposed in one of said plurality of vessel wells and a second optical pipe configured to receive light through a second portion of the vessel disposed in the one of said plurality of vessel wells.

* * * * *

UNITED STATES PATENT AND TRADEMARK OFFICE
CERTIFICATE OF CORRECTION

PATENT NO. : 6,900,059 B1
APPLICATION NO. : 09/721973
DATED : May 31, 2005
INVENTOR(S) : Alan Shinn et al.

It is certified that error appears in the above-identified patent and that said Letters Patent is hereby corrected as shown below:

In column 24, line 58, delete "82" and insert -- 83 --

Signed and Sealed this

Eighteenth Day of July, 2006

JON W. DUDAS
*Director of the United States Patent and Trademark Office*